United States Patent
Dutreix et al.

(10) Patent No.: US 10,821,128 B2
(45) Date of Patent: Nov. 3, 2020

(54) TREATMENT OF CANCER BY SYSTEMIC ADMINISTRATION OF DBAIT MOLECULES

(71) Applicants: ONXEO, Paris (FR); INSTITUT CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Marie Dutreix, L'Hay-les-Roses (FR); Nathalie Berthault, Boullay-les-Troux (FR)

(73) Assignees: ONXEO, Paris (FR); INSTITUT CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 149 days.

(21) Appl. No.: 16/081,045

(22) PCT Filed: Mar. 1, 2017

(86) PCT No.: PCT/EP2017/054702
§ 371 (c)(1),
(2) Date: Aug. 30, 2018

(87) PCT Pub. No.: WO2017/148976
PCT Pub. Date: Sep. 8, 2017

(65) Prior Publication Data
US 2019/0091254 A1 Mar. 28, 2019

(30) Foreign Application Priority Data
Mar. 1, 2016 (EP) .................................. 16305234

(51) Int. Cl.
| | | |
|---|---|---|
| *A61K 31/713* | (2006.01) | |
| *A61K 45/06* | (2006.01) | |
| *A61K 31/704* | (2006.01) | |
| *A61K 33/24* | (2019.01) | |
| *A61K 31/513* | (2006.01) | |
| *A61K 31/555* | (2006.01) | |
| *C12N 15/113* | (2010.01) | |
| *A61P 35/04* | (2006.01) | |
| *A61K 9/00* | (2006.01) | |

(52) U.S. Cl.
CPC .......... *A61K 31/713* (2013.01); *A61K 9/0019* (2013.01); *A61K 31/513* (2013.01); *A61K 31/555* (2013.01); *A61K 31/704* (2013.01); *A61K 33/24* (2013.01); *A61K 45/06* (2013.01); *A61P 35/04* (2018.01); *C12N 15/113* (2013.01); *C12N 2310/13* (2013.01); *C12N 2310/315* (2013.01); *C12N 2310/3183* (2013.01); *C12N 2310/3515* (2013.01); *C12N 2310/531* (2013.01)

(58) Field of Classification Search
None
See application file for complete search history.

(56) References Cited

U.S. PATENT DOCUMENTS 9,205,101 B2   12/2015  Dutreix et al.
2014/0100266 A1*  4/2014  Dutreix .................. A61K 31/00
                                                               514/44 R

FOREIGN PATENT DOCUMENTS

WO   WO 2012/163814   12/2012

OTHER PUBLICATIONS

Croset et al. Nucleic Acids Research 2013, vol. 41, pp. 7344-7355.*
O'Reilly et al. BBA Clinical 2015, vol. 3, pp. 257-275.*
Biau, J. et al. "A Preclinical Study Combining the DNA Repair Inhibitor Dbait with Radiotherapy for the Treatment of Melanoma" *Neoplasia*, Oct. 1, 2014, pp. 835-844, vol. 16, No. 10.
Devun, F. et al. "Antitumor effect of DNA repair inhibitor DT01 combined with TACE on VX2 rabbit liver tumors" *Journal of Vascular and Interventional Radiology*, Apr. 17, 2013, p. 1080, vol. 24, No. 7, Abstract No. LB08.
Dutreix, M. et al. "Abstract 4483: Preclinical study of Dbait, an inhibitor of three DNA repair pathways, in breast cancer treatment" Cancer Research, Apr. 1, 2013, retrieved on Apr. 19, 2017, retrieved from the internet: URL:http://cancerres.aacrjournals.org/content/73/8_Supplement/4483, pp. 1-3.
Herath, N. I. et al. "The DNA Repair Inhibitor DT01 as a Novel Therapeutic Strategy for Chemosensitization of Colorectal Liver Metastasis" *Molecular Cancer Therapeutics*, Jan. 2016, pp. 15-22, vol. 15, No. 1.
Sun, J- S. et al. "Gamma H2AX foci disorganization and anti-tumor activity by trapping DNA-PK with a double strand break mimicking agent" *Proceedings of the American Association for Cancer Research*, Apr. 18, 2007, pp. 470-471, vol. 48.
Reeder-Hayes, K. E. et al. "Clinical trials in triple negative breast cancer" *Breast Disease*, 2010-2011, pp. 123-136, vol. 32, Nos. 1-2.
Written Opinion in International Application No. PCT/EP2017/054702, dated May 11, 2017, pp. 1-8.

* cited by examiner

*Primary Examiner* — Tracy Vivlemore
(74) *Attorney, Agent, or Firm* — Saliwanchik, Lloyd & Eisenschenk

(57) ABSTRACT

The present invention relates to the use of a DBait molecules by systemic routes without any combination with an endosomolytic agent.

13 Claims, 3 Drawing Sheets
Specification includes a Sequence Listing.

TREATMENT OF CANCER BY SYSTEMIC ADMINISTRATION OF DBAIT MOLECULES

CROSS-REFERENCE TO RELATED APPLICATION

This application is the U.S. national stage application of International Patent Application No. PCT/EP2017/054702, filed Mar. 1, 2017.

The Sequence Listing for this application is labeled "Seq-List.txt" which was created on Aug. 22, 2018 and is 7 KB. The entire content of the sequence listing is incorporated herein by reference in its entirety.

FIELD OF THE INVENTION

The present invention relates to the field of oncology.

BACKGROUND OF THE INVENTION

Breast cancer is the most common female malignancy, with more than 1.7 million new cases diagnosed each year worldwide (Torre, Siegel, Ward, & Jemal, 2015). Molecular classification divides breast cancer in three major subgroups: LuminalA/B, HER2+ and Basal-like/Triple negative breast cancer (TNBC)(Vuong, Simpson, Green, Cummings, & Lakhani, 2014). Triple-negative breast cancer (TN BC) is an aggressive histological subtype with limited treatment options and very poor prognosis following progression after standard chemotherapeutic regimens. Resistance to current standard therapies such as anthracyclines or taxanes limits the available options for previously treated patients with metastatic TNBC to a small number of non-cross-resistant regimens, and there is currently no preferred standard chemotherapy. Platinum-based regimens are an emerging option for patients with TN BC with BRCA1 mutation.

Chemo-resistance presents a major obstacle to the efficacy of cancer treatment. DNA repair plays a key role in chemo-resistance by eliminating the damage induced on chromosomes by the chemotherapeutic agents and inhibitors of DNA repair pathways may provide novel opportunities for restoring tumor sensitivity to these treatments.

Dbait molecules are a new class of DNA repair inhibitors triggering false DNA damage signaling in cancer cells. These molecules are short double-stranded DNA with a free double strand blunt end, which target key damage signal transducers such as DNA dependent protein kinase (DNA-PK) and Poly-ADP-Ribo-Polymerase, triggering their activation and amplifying false damage signaling. Consequently, the recruitment of downstream DNA repair enzymes is impaired, inhibiting several DNA repair pathways such as homologous recombination, non-homologous end joining, base excision repair and single-strand break repair leading to an accumulation of unrepaired damage causing cell death.

Dbait molecules have been shown to be effective in combination with radiotherapy on several radio-resistant tumors, both in vitro and in vivo. In order to increase the efficiency of cellular uptake, the Dbait molecule was modified by covalently linking a cholesterol moiety to the 5'-end (DT01) (WO2011/161075; Berthault et al, 2011, Cancer gene therapy, 18, 695-706). It has been demonstrated that local administration of DT01 by intra-tumoral injection in association with radiotherapy, increases survival of xenografted human melanoma models (Biau et al, 2014, Neoplasia, 16, 835-844). However to date, the efficacy of systemic administration of DT01, alone or in association with chemotherapy, has not been investigated.

However, it has been shown that DT01 as an adjunct treatment enhances the therapeutic efficacy of transarterial chemoembolization (TACE) in a rabbit VX2 liver tumor model (Devun et al, Journal of Vascular and Interventional Radiology, 2013, 24, 1080) but TACE derives its beneficial effect by two primary mechanisms. Firstly, most tumors within the liver are supplied by the proper hepatic artery, so arterial embolization preferentially interrupts the tumor's blood supply and stalls growth until neovascularization. Secondly and most importantly, focused administration of chemotherapy allows for delivery of a higher dose to the tissue while simultaneously reducing systemic exposure, which is typically the dose limiting factor.

Moreover, the molecule DT01 was designed for being used in combination with an endosomolytic agent such as the chloroquine. The chloroquine facilitates the release of coDbait from endosomes into the cytosol and is described as necessary. It was thus shown that coDbait administered by subcutaneous and intratumoral injection in the presence of chloroquine and that concomitant chloroquine treatment was added to the protocol to increase coDbait uptake and efficacy resulting in an increase of the radiosensitivity of xenografted tumors by coDbait (Schlegel et al, 2012, Molecular Therapy-Nucleic Acids, 1, e33).

It should be further noted that some cancers, especially radioresistant or chemoresistant cancers such as triple-negative breast cancer (TNBC), remain difficult to treat and any improvement in their treatments is important.

SUMMARY OF THE INVENTION

Surprisingly, the inventors observed that the DBait molecules, especially those called coDBait which are conjugated to cholesterol, can be used efficiently for treating cancer, even resistant cancer, by systemic administration, especially intraperitoneal and intravenous administration, without any quinoline endosomlytic agent, especially chloroquine. Indeed, the same efficacy by these administration routes can be obtained with a dose which is only 2-5 fold higher and conjugated DBait has no toxicity. The efficacy of the conjugated DBait with intraperitoneal and intravenous administration has been shown with resistant cancers.

Therefore, the present invention relates to a nucleic acid molecule for use for treating cancer, wherein the nucleic acid molecule has one of the following formula:

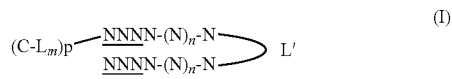

(I)

wherein N is a deoxynucleotide, n is an integer from 15 to 195, the underlined N refers to a nucleotide having or not a modified phosphodiester backbone, L' is a linker, C is the molecule facilitating endocytosis selected from a lipophilic molecule or a ligand which targets cell receptor enabling receptor mediated endocytosis, L is a linker, m is an integer being 0 or 1 and p is 1;
wherein the nucleic acid is to be used without combined administration of an endosomolytic agent;
wherein the nucleic acid is to be administered by a parenteral systemic route selected from intraperitoneal and intravenous routes.

Preferably, the nucleic acid of formula (I) has one or several of the following features:

- N is a deoxynucleotide selected from the group consisting of A (adenine), C (cytosine), T (thymine) and G (guanine) and selected so as to avoid occurrence of a CpG dinucleotide and to have less than 80% sequence identity to any gene in a human genome; and/or,
- the linked L' is selected from the group consisting of hexaethyleneglycol, tetradeoxythymidylate (T4) and 1,19-bis(phospho)-8-hydraza-2-hydroxy-4-oxa-9-oxo-nonadecane; and/or,
- m is 1 and L is a carboxamido polyethylene glycol, more preferably carboxamido triethylene or tetraethylene glycol; and/or,
- C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol or a tocopherol, still more preferably a cholesterol.

More preferably, the nucleic acid molecule has one of the following formulae:

(Ia)

SEQ ID NO: 6

C-L$_m$—ACGCACGGGTGTTGGGTCGTTTGTTCGGATCT
      TGCGTGCCCACAACCCAGCAAACAAGCCTAGA—L';

(Ib)

SEQ ID NO: 7

C-L$_m$—CGTAGGTCTGTTTGGTGGCTTTGCAGTGGCAC
      GCATCCAGACAAACCACCGAAACGTCACCGTG—L';

(Ic)

SEQ ID NO: 8

C-L$_m$—GCTAGGCTTGTTTGCTGGGTTGTAGGCACAGC
      CGATCCGAACAAACGACCCAACATCCGTGTCG—L';

(Id)

SEQ ID NO: 9

C-L$_m$—GCTGTGCCCACAACCCAGCAAACAAGCCTAGA
      CGACACGGGTGTTGGGTCGTTTGTTCGGATCT—L' and;

(Ie)

SEQ ID NO: 10

C-L$_m$—GCTAGGTCTGTTTGGTGGCTTTGCAGTGGCAC
      CGATCCAGACAAACCACCGAAACGTCACCGTG—L' wherein the underlined nucleotide refers to a nucleotide having or not a phosphorothioate or methylphosphonate backbone, the linked L' is selected from the group consisting of hexaethyleneglycol, tetradeoxythymidylate (T4) and 1,19-bis(phospho)-8-hydraza-2-hydroxy-4-oxa-9-oxo-nonadecane; m is 1 and L is a carboxamido oligoethylene glycol, C is selected from the group consisting of dioleoyl, octadecyl, folic acid, tocopherol and cholesterol;

wherein the nucleic acid is to be used without any combined administration of an endosomolytic agent, especially chloroquine; and wherein the nucleic acid is to be administered by a parenteral systemic route selected from intraperitoneal and intravenous routes.

Still more preferably, the nucleic acid is

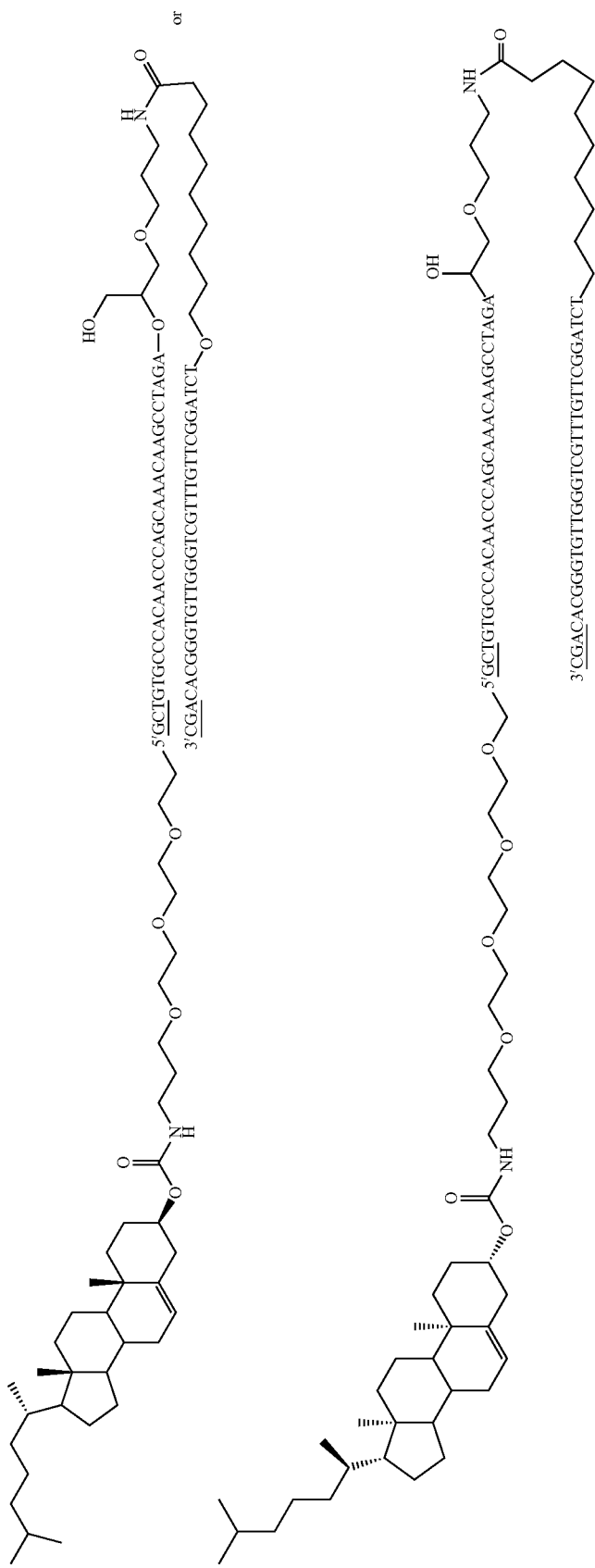

wherein the underlined nucleotide refers to a nucleotide having a phosphorothioate backbone.

Preferably, the nucleic acid is to be administered by intravenous route, for instance administered by injection, intravenous drip, bolus or pump.

Preferably, the cancer is a radioresistant or chemoresistant cancer. More preferably, it is selected from the group consisting of a triple-negative breast cancer (TNBC), a chemoresistant hepatocellular carcinoma (HCC), a chemoresistant ovarian cancer, a chemoresistant lung cancer, and a metastatic liver cancer. In a particular embodiment, the cancer is selected from the group consisting of a doxorubicin-resistant hepatocarcinoma (HCC), a platinum-resistant ovarian cancer, a platinum-resistant triple-negative breast cancer and a colorectal liver metastasis.

Preferably, the nucleic acid is to be used in combination with radiotherapy and/or chemotherapy. In one embodiment, the nucleic acid is to be used in combination with a DNA damaging agent. Preferably, the DNA damaging agent is selected from the group consisting of an inhibitor of topoisomerases I or II, a DNA crosslinker, a DNA alkylating agent, an anti-metabolic agent and inhibitors of the mitotic spindles. More preferably, the nucleic acid is to be used in combination with a chemotherapy selected from the group consisting of doxorubicin, oxaliplatin, carboplatin, cisplatin and 5-FU.

DETAILED DESCRIPTION OF THE INVENTION

The present invention relates to a nucleic acid molecule (coDBait) for use for treating cancer, wherein the nucleic acid molecule has one of the following formula:

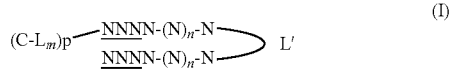

(I)

wherein N is a deoxynucleotide, n is an integer from 1 to 195, the underlined N refers to a nucleotide having or not a modified phosphodiester backbone, L' is a linker, C is the molecule facilitating endocytosis selected from a lipophilic molecule or a ligand which targets cell receptor enabling receptor mediated endocytosis, L is a linker, m is an integer being 0 or 1 and p is 1;
wherein the nucleic acid is to be used without combined administration of an endosomolytic agent;
wherein the nucleic acid is to be administered by a parenteral systemic route selected from intraperitoneal and intravenous routes.

When the absence of a quinoline endosomolytic agent is mentioned herein, it refers to the endosomolytic agent as defined WO2011/161075 in pages 26-28 of (incorporated herein by reference). In particular, the quinoline endosomolytic agent is the chloroquine. In particular, it means that the nucleic acid as described herein is not for simultaneous, separate or sequential use with any endosomolytic agent.

The present invention relates to
a nucleic acid molecule as defined herein or a pharmaceutical composition comprising it, and optionally a pharmaceutically acceptable carrier, in particular for use in the treatment of cancer without combined administration of an quinoline endosomolytic agent and wherein the pharmaceutical composition is to be administered by a parenteral systemic route selected from intraperitoneal and intravenous routes, optionally in combination with radiotherapy and/or a DNA-damaging anti-tumor agent;
the use of a nucleic acid molecule as defined herein or a pharmaceutical composition comprising it for the manufacture of a medicament for treating cancer, wherein the medicament is not used in combination with any quinoline endosomolytic agent and is to be administered by a parenteral systemic route selected from intraperitoneal and intravenous routes, optionally in combination with radiotherapy and/or a DNA-damaging anti-tumor agent;
a method for treating cancer in a subject, comprising administering a therapeutic effective amount of a nucleic acid molecule as defined herein or a pharmaceutical composition comprising it by a parenteral systemic route selected from intraperitoneal and intravenous routes but without any administration of a quinoline endosomolytic agent;
a pharmaceutical composition comprising a nucleic acid molecule as defined herein, a DNA-damaging anti-tumor agent, and a pharmaceutically acceptable carrier, in particular for use in the treatment of cancer without combined administration of an quinoline endosomolytic agent and wherein the pharmaceutical composition is to be administered by a parenteral systemic route selected from intraperitoneal and intravenous routes;
a pharmaceutical composition comprising a nucleic acid molecule as defined herein and a DNA-damaging anti-tumor agent for the manufacture of a medicament for treating cancer, wherein the medicament is not used in combination with any quinoline endosomolytic agent and is to be administered by a parenteral systemic route selected from intraperitoneal and intravenous routes;
a method for treating cancer in a subject, comprising administering a therapeutic effective amount of a pharmaceutical composition comprising a nucleic acid molecule as defined herein and a DNA-damaging anti-tumor agent by a parenteral systemic route selected from intraperitoneal and intravenous routes but without any administration of a quinoline endosomolytic agent, optionally in combination with radiotherapy and/or a DNA-damaging anti-tumor agent;
a product or kit containing (a) a nucleic acid molecule as defined herein, and optionally b) a DNA-damaging anti-tumor agent, as a combined preparation for simultaneous, separate or sequential use, in particular in the treatment of cancer without combined administration of an quinoline endosomolytic agent and wherein the pharmaceutical composition is to be administered by a parenteral systemic route selected from intraperitoneal and intravenous routes;
a method for treating a cancer in a subject in need thereof, comprising administering an effective amount of a pharmaceutical composition comprising a nucleic acid molecule as defined herein by a parenteral systemic route selected from intraperitoneal and intravenous routes but without any administration of a quinoline endosomolytic agent, and an effective amount of a pharmaceutical composition comprising a DNA-damaging anti-tumoral agent.

The terms "kit", "product" or "combined preparation", as used herein, defines especially a "kit of parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

Within the context of the invention, the term treatment denotes curative, symptomatic, and preventive treatment. Pharmaceutical compositions, kits, products and combined preparations of the invention can be used in humans with existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, ameliorating thereby the patients' condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition of the invention is administered in a therapeutically effective amount.

By "therapeutically effective amount" it is meant the quantity of the pharmaceutical composition of the invention which prevents, removes or reduces the deleterious effects of cancer in mammals, including humans, alone or in combination with the other active ingredients of the pharmaceutical composition, kit, product or combined preparation. It is understood that the administered dose may be lower for each compound in the composition to the "therapeutic effective amount" define for each compound used alone or in combination with other treatments than the combination described here. The "therapeutic effective amount" of the composition will be adapted by those skilled in the art according to the patient, the pathology, the mode of administration, etc.

Whenever within this whole specification "treatment of a cancer" or the like is mentioned with reference to the pharmaceutical composition of the invention, there is meant: a) a method for treating a cancer, said method comprising administering a pharmaceutical composition of the invention to a subject in need of such treatment; b) the use of a pharmaceutical composition of the invention for the treatment of a cancer; c) the use of a pharmaceutical composition of the invention for the manufacture of a medicament for the treatment of a cancer; and/or d) a pharmaceutical composition of the invention for use in the treatment a cancer.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with effectiveness of the biological activity of the active ingredient(s) and that is not toxic to the host to which it is administered. For example, for parental administration, the active compounds(s) may be formulated in a unit dosage form for injection in vehicles such as saline, dextrose solution, serum albumin and Ringer's solution.

The pharmaceutical composition can be formulated as solutions in pharmaceutically compatible solvents or as emulsions, suspensions or dispersions in suitable pharmaceutical solvents or vehicle in a way known in the art. Formulations suitable for parental administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions. Methods for the safe and effective administration of most of these chemotherapeutic agents are known to those skilled in the art. In addition, their administration is described in the standard literature.

Conjugated DBait Molecules, Called coDBait

The DBait molecules for use in the present invention can be described by the following formulae:

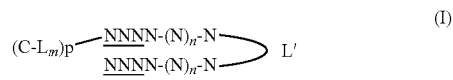

wherein N is a nucleotide, n is an integer of at least 1, the underlined N refers to a nucleotide having or not a modified phosphodiester backbone, L' is a linker, C is a molecule facilitating endocytosis, L is a linker, m is an integer being 0 or 1 and p is 1. Preferably, the underlined N refers to a nucleotide having a modified phosphodiester backbone.

In preferred embodiments, the molecule of formula (I) has one or several of the following features:

N is a deoxynucleotide, preferably selected from the group consisting of A (adenine), C (cytosine), T (thymine) and G (guanine) and selected so as to avoid occurrence of a CpG dinucleotide and to have less than 80% or 70%, even less than 60% or 50% sequence identity to any gene in a human genome; and/or, n is an integer from 15 to 195, from 15 to 95, from 19 to 95, from 21 to 95, from 27 to 95, from 15 to 45, from 19 to 45, from 21 to 45, or from 27 to 45. In a particularly preferred embodiment, n is 27; and/or, the underlined N refers to a nucleotide having or not a phosphorothioate or methylphosphonate backbone, more preferably a phosphorothioate backbone; preferably, the underlined N refers to a nucleotide having a modified phosphodiester backbone; and/or, the linked L' is selected from the group consisting of hexaethyleneglycol, tetradeoxythymidylate (T4) and 1,19-bis(phospho)-8-hydraza-2-hydroxy-4-oxa-9-oxo-nonadecane; and/or, m is 1 and L is a carboxamido polyethylene glycol, more preferably carboxamido triethylene or tetraethylene glycol; and/or, C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol or a tocopherol, still more preferably a cholesterol.

Preferably, C-Lm is a triethyleneglycol linker (10-O-[1-propyl-3-N-carbamoylcholesteryl]-triethyleneglycol radical. Alternatively, C-Lm is a tetraethyleneglycol linker (10-O-[1-propyl-3-N-carbamoylcholesteryl]-tetraethyleneglycol radical.

In a particular embodiment, the nucleic acid molecules can be Dbait molecules such as those extensively described in PCT patent applications WO2005/040378, WO2008/034866 and WO2008/084087, the disclosure of which is incorporated herein by reference.

Dbait molecules may be defined by a number of characteristics necessary for their therapeutic activity, such as their minimal length, the presence of at least one free end, and the presence of a double stranded portion, preferably a DNA double stranded portion. As will be discussed below, it is important to note that the precise nucleotide sequence of Dbait molecules does not impact on their activity. Furthermore, Dbait molecules may contain a modified and/or non-natural backbone.

Preferably, Dbait molecules are of non-human origin (i.e., their nucleotide sequence and/or conformation (e.g., hairpin) does not exist as such in a human cell), most preferably of synthetic origin. As the sequence of the Dbait molecules plays little, if any, role, Dbait molecules have preferably no significant degree of sequence homology or identity to known genes, promoters, enhancers, 5'- or 3'-upstream sequences, exons, introns, and the like. In other words, Dbait molecules have less than 80% or 70%, even less than 60% or 50% sequence identity to any gene in a human genome. Methods of determining sequence identity are well known in the art and include, e.g., Blast. Dbait molecules do not hybridize, under stringent conditions, with human genomic DNA. Typical stringent conditions are such that they allow the discrimination of fully complementary nucleic acids from partially complementary nucleic acids.

In addition, the sequence of the Dbait molecules is preferably devoid of CpG in order to avoid the well-known toll-like receptor-mediated immunological reactions.

The length of Dbait molecules may be variable, as long as it is sufficient to allow appropriate binding of Ku protein complex comprising Ku and DNA-PKcs proteins. It has been showed that the length of Dbait molecules must be greater than 20 bp, preferably about 32 bp, to ensure binding to such a Ku complex and allowing DNA-PKcs activation. Preferably, Dbait molecules comprise between 20-200 bp, more preferably 24-100 bp, still more preferably 26-100, and most preferably between 24-200, 25-200, 26-200, 27-200, 28-200, 30-200, 32-200, 24-100, 25-100, 26-100, 27-100, 28-100, 30-100, 32-200 or 32-100 bp. For instance, Dbait molecules comprise between 24-160, 26-150, 28-140, 28-200, 30-120, 32-200 or 32-100 bp. By "bp" is intended that the molecule comprise a double stranded portion of the indicated length.

In a particular embodiment, the Dbait molecules having a double stranded portion of at least 32 pb, or of about 32 bp, comprise the same nucleotide sequence than Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). Optionally, the Dbait molecules have the same nucleotide composition than Dbait32, Dbait32Ha, Dbait32Hb, Dbait32Hc or Dbait32Hd but their nucleotide sequence is different. Then, the Dbait molecules comprise one strand of the double stranded portion with 3 A, 6 C, 12 G and 11 T. Preferably, the sequence of the Dbait molecules does not contain any CpG dinucleotide.

Alternatively, the double stranded portion comprises at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a more particular embodiment, the double stranded portion consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

The nucleic acid as disclosed herein must have at least one free end, as a mimic of DSB.

In a particular embodiment, they contain only one free end. Preferably, Dbait molecules are made of hairpin nucleic acids with a double-stranded DNA stem and a loop. The loop can be a nucleic acid, or other chemical groups known by skilled person or a mixture thereof. A nucleotide linker may include from 2 to 10 nucleotides, preferably, 3, 4 or 5 nucleotides. Non-nucleotide linkers non exhaustively include abasic nucleotide, polyether, polyamine, polyamide, peptide, carbohydrate, lipid, polyhydrocarbon, or other polymeric compounds (e. g. oligoethylene glycols such as those having between 2 and 10 ethylene glycol units, preferably 4, 5, 6, 7 or 8 ethylene glycol units). A preferred linker is selected from the group consisting of hexaethyleneglycol, tetradeoxythymidylate (T4) and other linkers such as 1,19-bis(phospho)-8-hydraza-2-hydroxy-4-oxa-9-oxo-nonadecane. Accordingly, in a particular embodiment, the Dbait molecules can be a hairpin molecule having a double stranded portion or stem comprising at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) and a loop being a hexaethyleneglycol linker, a tetradeoxythymidylate linker (T4) or 1,19-bis(phospho)-8-hydraza-2-hydroxy-4-oxa-9-oxo-nonadecane. In a more particular embodiment, those Dbait molecules can have a double stranded portion consisting in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

Dbait molecules preferably comprise a 2'-deoxynucleotide backbone, and optionally comprise one or several (2, 3, 4, 5 or 6) modified nucleotides and/or nucleobases other than adenine, cytosine, guanine and thymine. Accordingly, the Dbait molecules are essentially a DNA structure. In particular, the double-strand portion or stem of the Dbait molecules is made of deoxyribonucleotides.

Preferred Dbait molecules comprise one or several chemically modified nucleotide(s) or group(s) at the end of one or of each strand, in particular in order to protect them from degradation. In a particular preferred embodiment, the free end(s) of the Dbait molecules is(are) protected by one, two or three modified phosphodiester backbones at the end of one or of each strand. Preferred chemical groups, in particular the modified phosphodiester backbone, comprise phosphorothioates. Alternatively, preferred Dbait have 3'-3' nucleotide linkage, or nucleotides with methylphosphonate backbone. Other modified backbones are well known in the art and comprise phosphoramidates, morpholino nucleic acid, 2'-0,4'-C methylene/ethylene bridged locked nucleic acid, peptide nucleic acid (PNA), and short chain alkyl, or cycloalkyl intersugar linkages or short chain heteroatomic or heterocyclic intrasugar linkages of variable length, or any modified nucleotides known by skilled person. In a first preferred embodiment, the Dbait molecules have the free end(s) protected by one, two or three modified phosphodiester backbones at the end of one or of each strand, more preferably by three modified phosphodiester backbones (in particular phosphorothioate or methylphosphonate) at least at the 3' end, but still more preferably at both 5' and 3' ends.

In a most preferred embodiment, the Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4) and 1,19-bis(phospho)-8-hydraza-2-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links).

Said nucleic acid molecules are made by chemical synthesis, semi-biosynthesis or biosynthesis, any method of amplification, followed by any extraction and preparation methods and any chemical modification. Linkers are provided so as to be incorporable by standard nucleic acid chemical synthesis.

More preferably, nucleic acid molecules are manufactured by specially designed convergent synthesis: two complementary strands are prepared by standard nucleic acid chemical synthesis with the incorporation of appropriate linker precursor, after their purification, they are covalently coupled together.

The molecules facilitating endocytosis are conjugated to Dbait molecules, preferably through a linker. Any linker known in the art may be used to covalently attach the molecule facilitating endocytosis to Dbait molecules For instance, WO09/126933 provides a broad review of convenient linkers pages 38-45. The linker can be non-exhaustively, aliphatic chain, polyether, polyamine, polyamide, peptide, carbohydrate, lipid, polyhydrocarbon, or other polymeric compounds (e. g. oligoethylene glycols such as those having between 2 and 10 ethylene glycol units, preferably 3, 4, 5, 6, 7 or 8 ethylene glycol units, still more preferably 6 ethylene glycol units), as well as incorporating any bonds that may be break down by chemical or enzymatical way, such as a disulfide linkage, a protected disulfide linkage, an acid labile linkage (e.g., hydrazone linkage), an ester linkage, an ortho ester linkage, a phosphonamide linkage, a biocleavable peptide linkage, an azo linkage or an aldehyde linkage. Such cleavable linkers are detailed in WO2007/040469 pages 12-14, in WO2008/022309 pages 22-28.

In a particular embodiment, the nucleic acid molecule can be linked to one molecule facilitating endocytosis. Alternatively, several molecules facilitating endocytosis (e.g., two, three or four) can be attached to one nucleic acid molecule.

In a specific embodiment, the linker between the molecule facilitating endocytosis, in particular cholesterol, and nucleic acid molecule is $CO-NH-(CH_2-CH_2-O)_n$, wherein n is an integer from 1 to 10, preferably n being selected from the group consisting of 3, 4, 5 and 6. In a very particular embodiment, the linker is $CO-NH-(CH_2-CH_2-O)_4$ (carboxamido tetraethylene glycol) or $CO-NH-(CH_2-CH_2-O)_3$ (carboxamido triethylene glycol). The linker can be linked to nucleic acid molecules at any convenient position which does not modify the activity of the nucleic acid molecules. In particular, the linker can be linked at the 5' end. Therefore, in a preferred embodiment, the contemplated conjugated Dbait molecule is a Dbait molecule having a hairpin structure and being conjugated to the molecule facilitating endocytosis, preferably through a linker, at its 5' end.

In another specific embodiment, the linker between the molecule facilitating endocytosis, in particular cholesterol, and nucleic acid molecule is dialkyl-disulfide {e.g., $(CH_2)_r-S-S-(CH_2)_s$ with r and s being integer from 1 to 10, preferably from 3 to 8, for instance 6}.

In a most preferred embodiment, the conjugated Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4) and 1,19-bis(phospho)-8-hydraza-2-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links) and said Dbait molecule being conjugated to a cholesterol at its 5' end, preferably through a linker (e.g. carboxamido oligoethylene glycol, preferably carboxamido triethylene or tetraethylene glycol).

In a preferred embodiment, NNNN—(N)$_n$—N comprises at least 6, 8, 10, 12, 14, 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) or consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a particular embodiment, NNNN—(N)$_n$—N comprises or consists in Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5), more preferably Dbait32Hc (SEQ ID No 4).

According, the conjugated Dbait molecule or hairpin nucleic acid molecule may be selected from the group consisting of:

(Ia)

with NNNN-(N)$_n$-N being SEQ ID No 1

(C—L$_m$)p—ACGCACGGGTGTTGGGTCGTTTGTTCGGATCT / TGCGTGCCCACAACCCAGCAAACAAGCCTAGA—L'   (SEQ ID NO: 6)

(Ib)

with NNNN-(N)$_n$-N being SEQ ID No 2

(C—L$_m$)p—CGTAGGTCTGTTTGGTGGCTTTGCAGTGGCAC / GCATCCAGACAAACCACCGAAACGTCACCGTG—L'   (SEQ ID NO: 7)

(Ic)

with NNNN-(N)$_n$-N being SEQ ID No 3

(C—L$_m$)p—GCTAGGCTTGTTTGCTGGGTTGTAGGCACAGC / CGATCCGAACAAACGACCCAACATCCGTGTCG—L'   (SEQ ID NO: 8)

-continued (Id)

with NNNN-(N)$_n$-N being SEQ ID No 4

(C—L$_m$)p —[GCTGTGCCCACAACCCAGCAAACAAGCCTAGA / CGACACGGGTGTTGGGTCGTTTGTTCGGATCT]— L'  (SEQ ID NO: 9)

(Id)

with NNNN-(N)$_n$-N being SEQ ID No 5

C—L$_m$ —[GCTAGGTCTGTTTGGTGGCTTTGCAGTGGCAC / CGATCCAGACAAACCACCGAAACGTCACCGTG]— L'  (SEQ ID NO: 10)

with the same definition than formulae (I) for L, L', C, p and m.

In preferred embodiments, the molecule of formulae (Ia), (Ib), (Ic), (Id), and (Ie), has one or several of the following features:
- the underlined nucleotide refers to a nucleotide having or not a phosphorothioate or methylphosphonate backbone, more preferably a phosphorothioate backbone; preferably, the underlined nucleotide refers to a nucleotide having a phosphorothioate or methylphosphonate backbone, more preferably a phosphorothioate backbone; and/or,
- the linked L' is selected from the group consisting of hexaethyleneglycol, tetradeoxythymidylate (T4) and 1,19-bis(phospho)-8-hydraza-2-hydroxy-4-oxa-9-oxo-nonadecane; and/or,
- m is 1 and L is a carboxamido polyethylene glycol, more preferably carboxamido triethylene or tetraethylene glycol; and/or,
- p is 1; and/or,
- C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol.

Preferably, C-Lm is a triethyleneglycol linker (10-O-[1-propyl-3-N-carbamoylcholesteryl]-triethyleneglycol radical) or a tetraethyleneglycol linker (10-O-[1-propyl-3-N-carbamoylcholesteryl]-tetraethyleneglycol radical).

In a specific embodiment of the Dbait molecules or hairpin nucleic acid molecules of formulae (I), (Ia), (Ib), (Ic), (Id), and (Ie), L' is preferably selected from the group consisting of hexaethyleneglycol, tetradeoxythymidylate (T4) and 1,19-bis(phospho)-8-hydraza-2-hydroxy-4-oxa-9-oxo-nonadecane.

In a specific embodiment of the Dbait molecules or hairpin nucleic acid molecules of formulae (I), (Ia), (Ib), (Ic), (Id), and (Ie), with C being cholesterol, C-L$_m$ is the radical

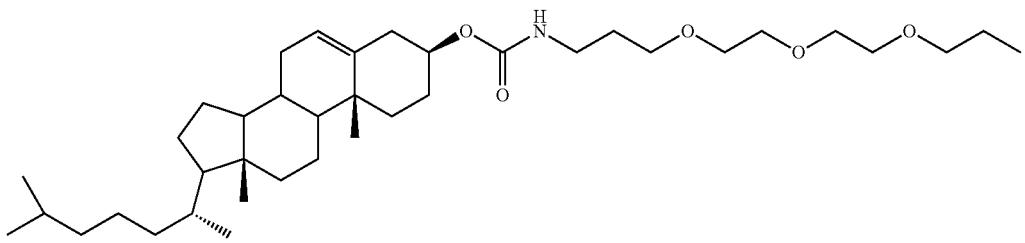 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

In a preferred embodiment, the conjugated Dbait molecule or hairpin nucleic acid molecule is selected from the group consisting of (I), (Ia), (Ib), (Ic), (Id), and (Ie), wherein C-L$_m$ being the radical

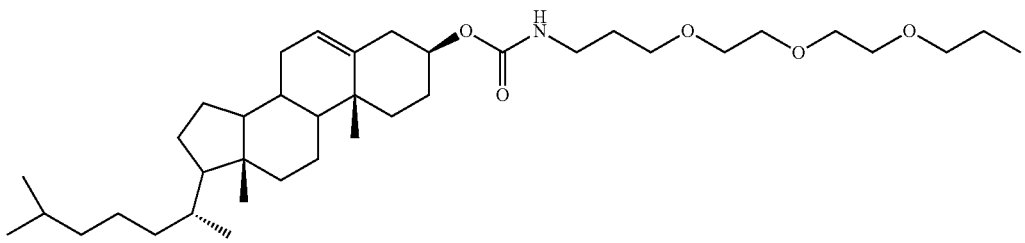 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

and wherein L' is preferably selected from the group consisting of hexaethyleneglycol, tetradeoxythymidylate (T4) and 1,19-bis(phospho)-8-hydraza-2-hydroxy-4-oxa-9-oxononadecane, more preferably 1,19-bis(phospho)-8-hydraza-2-hydroxy-4-oxa-9-oxo-nonadecane.

In a very specific embodiment, the Dbait molecule or hairpin nucleic acid molecule has the following formula

(IId)

wherein C-L$_m$ is a tetraethyleneglycol linker (10-O-[1-propyl-3-N-carbamoylcholesteryl]-tetraethyleneglycol radical, and L' is 1,19-bis(phospho)-8-hydraza-2-hydroxy-4-oxa-9-oxo-nonadecane and wherein the underlined nucleotides have a phosphorothioate backbone.

Accordingly, the molecule has the following structure and it is referred thereto in the Example section as "coDbait" or "DT01".

SEQ ID No 11

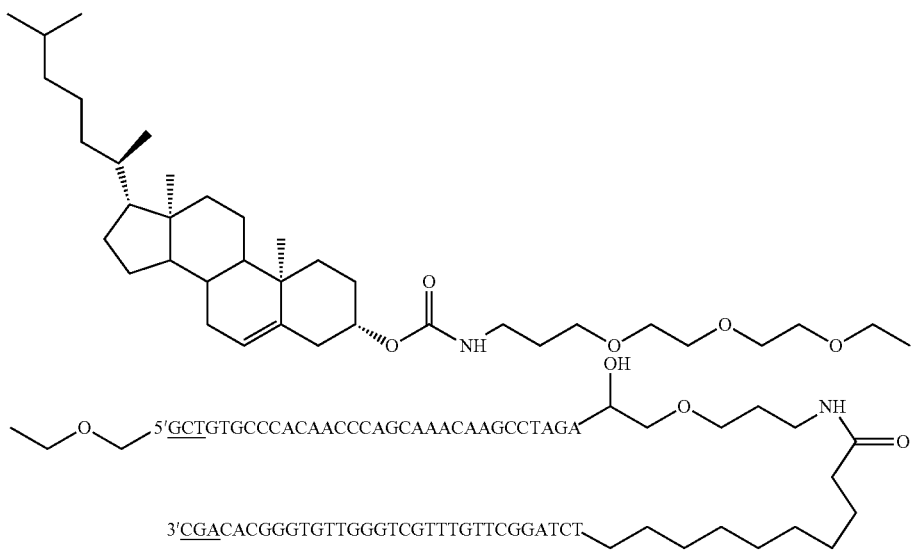

Another representation of this molecule is shown below:

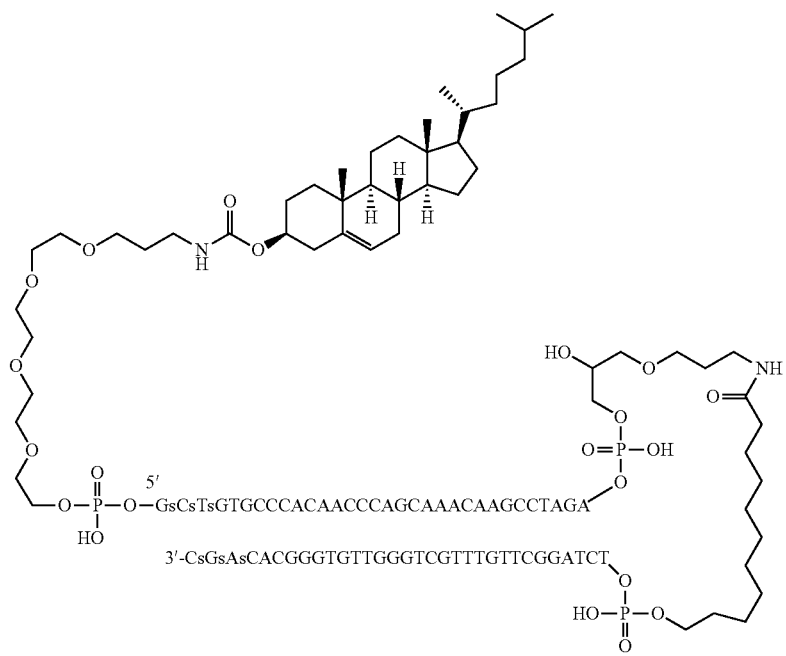

An alternative molecule is the following:

SEQ ID No 9

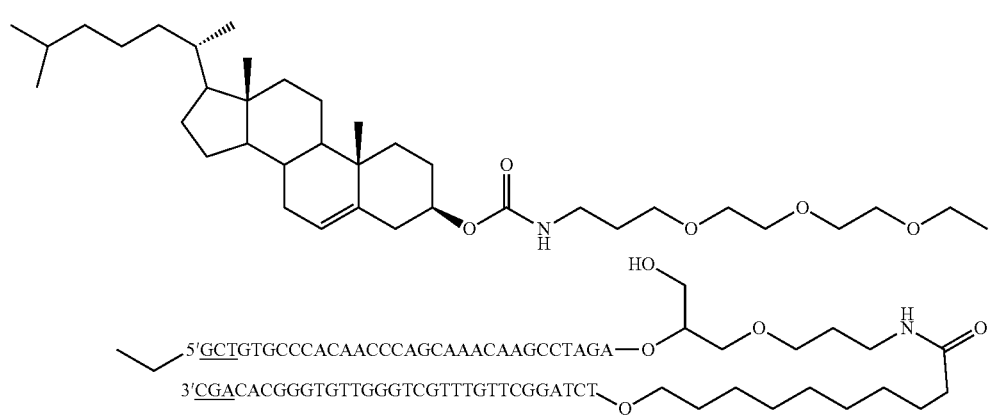

In another preferred embodiment, the nucleic acid molecule has one of the following formulae

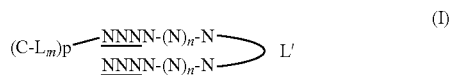   (I)

wherein N is a deoxynucleotide, n is an integer from 1 to 195, the underlined N refers to a nucleotide having or not a modified phosphodiester backbone, L' is a linker, C is a cholesterol, L is a linker, m is an integer being 0 or 1, and p is 1. Preferably, the underlined N refers to a nucleotide having a modified phosphodiester backbone.

DNA Damaging Treatment

In addition to the conjugated Dbait molecules, the treatment may also further comprise an antitumor treatment, preferably a treatment by a DNA damaging agent or radiotherapy. The DNA-damaging treatment can be radiotherapy or chemotherapy with a DNA-damaging antitumor agent, or a combination thereof.

DNA strand breakage can be achieved by ionized radiation (radiotherapy). Radiotherapy includes, but is not limited to, γ-rays, X-rays, and/or the directed delivery of radioisotopes to tumor cells. Other radiotherapies include microwaves and UV-irradiation. Other approaches to radiation therapy are also contemplated in the present invention.

The DNA-damaging antitumor agent is preferably selected from the group consisting of an inhibitor of topoisomerases I or II, a DNA crosslinker, a DNA alkylating agent, an anti-metabolic agent and inhibitors of the mitotic spindles.

Inhibitors of topoisomerases I and/or II include, but are not limited to, etoposide, topotecan, camptothecin, irinotecan, amsacrine, intoplicine, anthracyclines such as doxorubicin, epirubicine, daunorubicine, idanrubicine and mitoxantrone. Inhibitors of Topoisomerase I and II include, but are not limited to, intoplecin. In a preferred embodiment, the DNA-damaging antitumor agent is doxorubicin.

DNA crosslinkers include, but are not limited to, cisplatin, carboplatin and oxaliplatin. In a preferred embodiment, the DNA-damaging antitumor agent is selected from the group consisting of carboplatin and oxaliplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-fluorouracil (5-FU), gemcitabine and capecitabine.

The DNA-damaging anti-tumor agent can be alkylating agents including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN®), Ifosfamide, Melphalan, Chlorambucil, Pipobroman, Triethylenemelamine, Triethylenethiophosphoramine, Busulfan, Carmustine, Lomustine, Fotemustine, cisplatin, carboplatin, oxaliplatin, thiotepa, Streptozocin, Dacarbazine, and Temozolomide.

Inhibitors of the mitotic spindles include, but are not limited to, paclitaxel, docetaxel, vinorelbine, larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called Taxoprexin®), and MAC-321 (WYETH). Also see the review of Hennenfent & Govindan (2006, Annals of Oncology, 17, 735-749).

Preferably, the DNA-damaging antitumor agent is an inhibitor of topoisomerases I and/or II, a DNA crosslinker, an anti-metabolic agent or a combination thereof. In a preferred embodiment, the DNA-damaging antitumor agent is selected from the group consisting of doxorubicin, 5-FU, carboplatin and oxaliplatin or a combination thereof. In a most preferred embodiment, the conjugated DBait is DT01 and the DNA-damaging antitumor agent is selected from the group consisting of doxorubicin, carboplatin, 5-FU and oxaliplatin.

Cancers or Tumors to be Treated

The pharmaceutical compositions and the products, kits or combined preparation described in the invention can be used for treating cancer in a subject.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), chronic lymphocytic leukemia, mastocytosis and any symptom associated with mastocytosis.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ALL).

Various cancers are also encompassed by the scope of the invention, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, retinoblastoma, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

In a preferred embodiment of the present invention, the cancer is a solid tumor. The term "solid tumor" especially means breast cancer, ovarian cancer, cancer of the colon and generally the GI (gastro-intestinal) tract, cervix cancer, lung cancer, in particular small-cell lung cancer, and non-smallcell lung cancer, head and neck cancer, bladder cancer, cancer of the prostate or Kaposi's sarcoma.

The pharmaceutical compositions and the products, kits or combined preparations described in the invention may be useful for inhibiting the growth of solid tumors, decreasing the tumor volume, preventing the metastatic spread of tumors and the growth or development of micrometastases. The pharmaceutical compositions and the products, kits or combined preparations described in the invention are in particular suitable for the treatment of poor prognosis patients or of radio- or chemo-resistant tumors.

In one embodiment, the cancer can be selected from melanoma, glioblastoma, breast cancer, colon cancer, lung cancer, gastrointestinal cancer, liver cancer and head and neck cancer.

In a preferred embodiment, the cancer is a radioresistant or chemoresistant cancer. More particularly, the cancer is selected from the group consisting of a radioresistant melanoma, a triple-negative breast cancer (TNBC), a chemoresistant hepatocellular carcinoma (HCC), a chemoresistant lung cancer, a chemoresistant ovarian cancer and a metastatic liver cancer. More specifically, the cancer is selected from the group consisting of a doxorubicin-resistant hepatocarcinoma (HCC), a platinum-resistant triple-negative breast cancer, a platinum-resistant ovarian cancer and a colorectal liver metastasis.

In a specific embodiment, the present invention relates to the use of conjugated DBait molecules for the treatment of colorectal carcinoma in combination with oxaliplatin and 5-FU. Preferably, the colorectal carcinoma is metastatic, more preferably with metastasis in the liver and/or peritoneum.

In a very specific embodiment, the present invention relates to the use of conjugated DBait molecules for the treatment of radioresistant or chemoresistant cancer which is not localized into the abdominal cavity. Such cancers do not encompass colorectal carcinoma (e.g. CRC metastasis of the liver and the peritoneum) accordingly. More particularly, the cancer is selected from the group consisting of a TNBC and a chemoresistant ovarian cancer. More specifically, the cancer is selected from the group consisting of a platinum-resistant TNBC and a platinum-resistant ovarian cancer.

In a further embodiment, the present invention relates to the use of conjugated DBait molecules for the treatment of triple negative breast cancer. More specifically, the conjugated DBait molecules is used in combination with platinum-containing anti-cancer drugs, especially selected from cisplatin, oxaliplatin and carboplatin. In a specific embodiment, the present invention relates to the use of conjugated DBait molecules for the treatment of triple-negative breast cancer (TNBC) in combination with carboplatin. Optionally, the treatment can be combined with radiotherapy.

Regimen, Dosages and Administration Routes

The effective dosage of each of the combination partners employed in the combined preparation of the invention may vary depending on the particular compound or pharmaceutical composition employed, the mode of administration, the condition being treated, the severity of the condition being treated. Thus, the dosage regimen of the combined preparation of the invention is selected in accordance with a variety of factors including the route of administration and the patient status. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

When a DNA-damaging antitumor agent is used in combination with the conjugated Dbait molecule, the DNA-damaging antitumor agent and the conjugated Dbait molecules may be administered by the same route or by distinct routes. The administration route for the DNA-damaging antitumor agent may be oral, parenteral, intravenous, intratumoral, subcutaneous, intracranial, intraartery, topical, rectal, transdermal, intradermal, nasal, intramuscular, intraosseous, and the like.

The conjugated Dbait molecules is to be administered before and/or simultaneously with and/or after the irradiation and/or the administration of the DNA-damaging antitumor agent, more preferably before and/or simultaneously with the irradiation and/or the administration of the DNA-damaging antitumor agent. The irradiation and/or the administration of the DNA-damaging antitumor agent is performed so as the conjugated Dbait molecules are present in the tumoral cells when the irradiation is applied or when the DNA-damaging antitumor agent reach the tumoral cells. The physician, clinician or veterinarian of ordinary skill can determine the regimen based on the active ingredients, their kinetics of availability to target sites or their pharmacokinetic profiles in plasma. Preliminary results indicate that conjugated Dbait molecules stay active during one day. In a first preferred embodiment, the irradiation is to be applied or the DNA-damaging antitumor agent is to be administered at the beginning of the treatment with conjugated Dbait molecules or after the treatment with conjugated Dbait molecules. For instance, the irradiation is to be applied or the DNA-damaging antitumor agent is to be administered 3-24 h after the beginning of the treatment with conjugated Dbait molecules. The DNA-damaging antitumor agent and conjugated Dbait molecules may also be simultaneously administered.

Once the treatment by radiotherapy or with the DNA-damaging antitumor agent has begun, the treatment with the conjugated Dbait molecules can continue as long as the treatment by radiotherapy or with the DNA-damaging antitumor agent is to be applied or administered. Alternatively, the treatment with the conjugated Dbait molecules can also end.

For conjugated Dbait molecules, the effective dosage of the DNA-damaging antitumor agent employed in the combined preparation, kit or product of the invention may vary depending on the mode of administration, the condition being treated, the severity of the condition being treated. Thus, the dosage regimen of the conjugated Dbait molecules is selected in accordance with a variety of factors including the route of administration and the patient status. A physician, clinician or veterinarian of ordinary skill can readily determine and prescribe the effective amount of the conjugated Dbait molecules required to prevent, counter or arrest the progress of the cancer, in particular in combination with the selected DNA damaging treatment.

The one skilled in the art can adapt the amount in order to obtain an efficient amount of the conjugated Dbait molecules in the tumor of at least 0.01 mg per 1 $cm^3$ of tumor, preferably 0.1-40 mg per 1 $cm^3$ of tumor, most preferably 1-20 mg per 1 $cm^3$ of tumor, in particular in a daily treatment protocol or in a weekly treatment protocol. For instance, for an intravenous or intraperitoneal route, the efficient amount or unit dosage of the conjugated Dbait molecules may be of 0.1 to 100 mg, preferably of 4 to 40 mg. Accordingly, the efficient amount or unit dosage of the conjugated Dbait molecules may be of 0.06 to 0.6 mg/kg of patient. Of course, the dosage and the regimen can be adapted by the one skilled in art in consideration of the chemotherapy and/or radiotherapy regimen.

For radiotherapy, any radiotherapy regimen known in the art may be used, in particular stereotactic irradiation (e.g., 15 Gy) or a fractionated irradiation. The use of a fractionated irradiation may be particularly efficient, for instance irradiation may applied every day or every 2-5 days, preferably every 3-4 days, in a period of one, two, three, four, five or six weeks. The irradiation may be from 1 to 10 Gy, preferably from 2 to 5 Gy, in particular 2, 3, 4 or 5 Gy. For instance, fractionated irradiation of 15×2Gy in six weeks, or of 4 to 6×5Gy in two weeks may be contemplated. In a preferred embodiment, the contemplated radiotherapy is a protocol with 4 irradiations of 5 Gy in two weeks. Different regimens or conditions of combined treatments of cancer with irradiation and Dbait molecules have been tested and allowed to demonstrate the radio-sensibilization of tumors by Dbait molecules depends on the doses of Dbait molecules but not of the irradiation doses.

For chemotherapy, the effective dosage of the DNA-damaging antitumor agent employed in the combined preparation, kit or product of the invention or in combination with the composition of the invention may vary depending on the particular DNA-damaging antitumor agent employed, the mode of administration, the condition being treated, the severity of the condition being treated. Thus, the dosage regimen of the DNA-damaging antitumor agent is selected in accordance with a variety of factors including the route of administration and the patient status. A physician, clinician or veterinarian of ordinary skill can readily determine and prescribe the effective amount of the DNA-damaging antitumor agent required to prevent, counter or arrest the progress of the cancer.

The treatment may include one or several cycles, for instance two to ten cycles, in particular two, three, four or five cycles. The cycles may be continued or separated. For instance, each cycle is separated by a period of time of one to eight weeks, preferably three to four weeks.

Further aspects and advantages of the present invention will be disclosed in the following experimental section, which should be regarded as illustrative and not limiting the scope of the present application. A number of references are cited in the present specification; each of these cited references is incorporated herein by reference.

EXAMPLES

Figure 1:
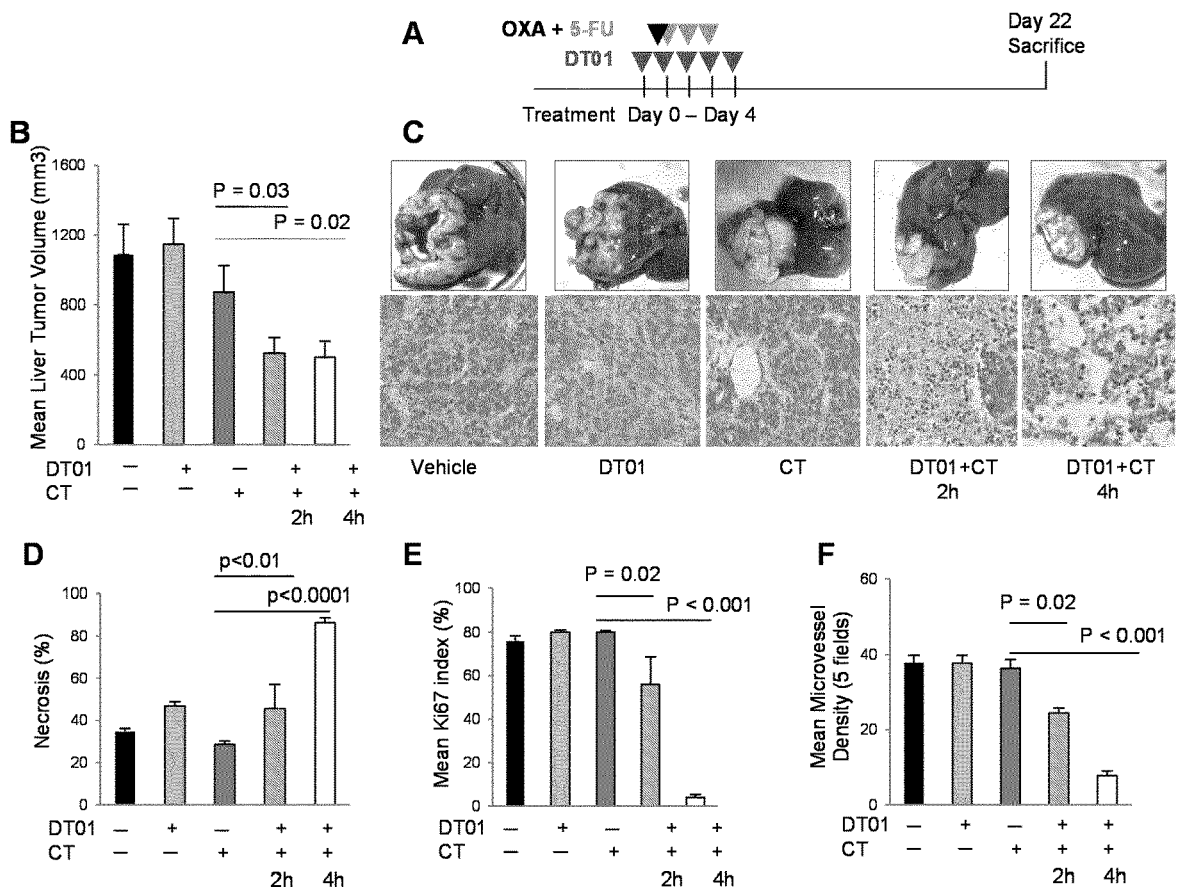
FIG. 1: DT01 significantly increases sensitivity to CT in a CRC (HT29) liver metastatic model Intrahepatic tumor bearing NMRI$^{NU/NU}$ mice were treated as described in the Material and Methods, and sacrificed 22 days post treatment. Livers were sampled for macroscopic and microscopic examination. (A) Sequence of DT01 and CT therapy. CT was administered 2 or 4 hours post DT01 treatment. (B) Mean liver tumor volume (mm$^3$) in each treatment group. (C) Representative macroscopic and HES sections of liver tumors in each group. (D) Tumor necrotic component assessed through HES staining. Necrosis is expressed as a proportion (%) of the total tumor surface of the tissue section analyzed. (E-F) Immunohistochemistry. Proliferation of the viable tumor component and the average micro-vessel density were determined by Ki67 (D) and CD31 (E) staining, respectively. Results are expressed as an average±SEM.

Example 1: DT01 as a Novel Therapeutic Strategy for Chemo-Sensitization of Colorectal Liver Metastasis Metastatic liver disease from colorectal cancer (CRC) is a significant clinical problem. This is mainly attributed to non-resectable metastases that frequently display low sensitivities to available chemotherapies and develop drug resistance partly via hyperactivation of some DNA repair functions. Combined therapies have shown some disease control however, there is still a need for more efficient chemotherapies to achieve eradication of CRC liver metastasis.

The inventors investigated the tolerance and efficacy of Dbait in association with conventional chemotherapy. In vitro, Dbait treatment increases sensitivity of HT29 and HCT116 CRC cell lines. In vivo, the pharmacokinetics, biodistribution and the efficacy of the cholesterol conjugated clinical form of Dbait, DT01, were assessed. The chemo-sensitizing abilities of DT01 were evaluated in association with oxaliplatin and 5-fluorouracil in intrahepatic HT29 xenografted mice used as a model for CRC liver metastasis. The high uptake of DT01 indicates that the liver is a specific target. The inventors demonstrated significant anti-tumor efficacy in a liver metastasis model with DT01 treatment in combination with oxaliplatin and 5-fluorouracil (mean: 501 vs 872 mm$^2$, p=0.02) compared to chemotherapy alone. The decrease in tumor volume is further associated with significant histological changes in necrosis, proliferation, angiogenesis and apoptosis. Repeated cycles of DT01 do not increase chemotherapy toxicity. Combining DT01 with conventional chemotherapy may prove to be a safe and effective therapeutic strategy in the treatment of metastatic liver cancer.

The aims of this study were to firstly demonstrate the efficacy of DT01 in vitro, secondly to assess the pharmacokinetics and the distribution of DT01 in the liver, and thirdly to demonstrate the concomitant impact of systemic DT01 administration in combination with conventional chemotherapy (oxaliplatin with 5'-fluorouracil) in a CRC metastatic liver tumor model.

Results

Dbait Treatment Increases Sensitivity of Colon Cancer Cell Lines to Chemotherapy The inventors have previously shown that Dbait acts by activating DNA-PK kinase, which phosphorylate numerous targets including the histone variant H2AX. They first confirmed the activity of Dbait in two CRC cell lines (HCT116 and HT29) by monitoring the pan-nuclear phosphorylation of H2AX.

To first investigate the effects of Dbait on cell survival to chemotherapy, the inventors determined the number of living cells, at different time points after treatment with Dbait or oxaliplatin (OXA) and 5-fluorouracil (5-FU) or a combination of Dbait with chemotherapy (CT) (FIG. 1B). As already observed in fibroblasts (Quanz, 2009, PloS one, 4, e6298), Dbait alone appears to have no effect on cell proliferation in both cell lines. Treatment with OXA and 5-FU resulted in a decrease in cell proliferation. However, the level of proliferation was significantly reduced by day 9 in cells transfected with Dbait prior to chemotherapy treatment in both HCT116 and HT29 cell lines compared to chemotherapy alone ($p<0.001$ and $p<0.02$, respectively). These differences become apparent particularly at later time points (>5 days after treatment) indicating that the increase of efficacy with Dbait may be a slow process.

To confirm the chemosensitization effect of Dbait in combination with OXA and 5-FU, clonogenic survival assays were performed on HCT116 and HT29. HCT116 cells showed approximately 30% ($p<0.01$) lethality after Dbait treatment alone revealing their dependency in repair activity for survival whereas no significant effect was noted in HT29. Since the sensitivity of HCT116 to Dbait was not detected during the first 8 days of proliferation, this result suggests that the cells growing with Dbait accumulate lethal lesions that impair their survival later on. Treatment with chemotherapy alone (OXA/5-FU) resulted in a significant decrease in the survival of HCT116 ($p<0.001$) whereas only a trend was observed with the HT29 cell line ($p=0.08$). However, combination of Dbait with chemotherapy resulted in a significant reduction in survival in both cell lines ($p=0.05$). HCT116 and HT29 differ by many parameters including their P53 status (HCT116 being proficient whereas HT29 is mutated). In this instance, despite some differences in their sensitivity to standalone Dbait treatment both cell lines were equally sensitive to the combination of CT with Dbait.

Pharmacokinetic and Biodistribution Analyses of Intraperitoneal Vs Intravenous Administration of DT01

To avoid transfectant adjuvant toxicity, all in vivo studies were performed with DT01, a Dbait-cholesterol conjugate facilitating the cellular uptake of these molecules without added toxicity. To determine the best route for systemic administration of DT01 mice were treated with either a single intraperitoneal (IP) or an intravenous (IV) dose of 5 mg of DT01. IP administration resulted in a $C_{max}$ of 578 µg/ml, a $T_{max}$ of 1 hour and an $AUC_{0-6}$ of 799 whereas IV led to a $C_{max}$ of 1,917 µg/ml, a $T_{max}$ of 0.08 hours and an $AUC_{0-6}$ of 799. Pharmacokinetic analyses revealed that following IP injection, the plasmatic exposure of DT01 was longer than that of IV bolus injection with an AUC corresponding to approximately 70% of the AUC with IV administration.

The inventors used a fluorescent labelled cy5-DT01 molecule to monitor the biodistribution in excised whole-organs. Both cy5-DT01 and DT01 have similar properties in terms of pharmacokinetics and DNA-PK activation. The maximal DT01 fluorescence was observed in the liver, intestines, and the kidneys by both routes with the highest intensities observed in the liver and intestines following IP administration. The high fluorescence emitted by the kidneys and urine observed in mice suggest that DT01 is preferentially eliminated by the kidneys. Although there was no measurable DT01 in the blood 6 hours after injection, significant amounts of DT01 were still detectable in the liver indicating a specific retention in this organ.

As already demonstrated in vitro, DT01 activation of DNA-PK in tissue can be revealed by the phosphorylation of the histone H2AX. The inventors monitored DT01 activity by analyzing distribution of H2AX phosphorylation in livers bearing HT29 grafted tumors. Interestingly, a high level of γ-H2AX was specifically observed in the tumor and not in the surrounding healthy tissues indicating a preferential uptake or activity of the DT01 molecules in the tumor cells of the liver.

DT01 Significantly Increases Sensitivity to OXA and 5-FU In Vivo

To explore the interest of associating DT01 with the frontline treatment for metastatic CRC, the inventors used a HT29 xenografted liver tumor model, since previous reports and the in vitro data demonstrate this line to be highly chemo-resistant mainly due to the V600E BRAF mutation. The animals were treated with OXA and 5-FU, a treatment close to the traditional FOLFOX protocol for patients, using two different schedules based on biodistribution data (FIG. 1A). The two schedules consisted of either two or four-hour intervals between the two treatments, since the maximum DT01 levels in the liver were observed at one and three hours after treatment.

As previously observed in vitro, the tumors were highly resistant to CT alone and DT01 had only a moderate effect when administered alone (FIGS. 1B, 1C). Interestingly, the association of DT01 to OXA and 5-FU significantly decreased the liver tumor size in both combination treated groups compared to CT alone when administered at two (mean volume: 525.80 vs 872.01 mm$^2$, $p=0.03$) and four hours (mean volume: 501.05 vs 872.01 mm$^2$, $p=0.02$) before CT (FIGS. 1B, 1C). This effect was not observed when DT01 was associated with a single chemotherapy agent, either OXA or 5-FU. Detailed blinded histological analyses including measures of the viable tumor area, necrosis and apoptosis were assessed in haematoxylin-eosin-saffron (HES) stained sections, by an experienced pathologist. Both groups with DT01 and CT combined treatment showed higher treatment efficacy than the groups receiving single treatment, with a marked increase in necrosis in the group treated with a four-hour interval between CT and DT01 ($p<0.0001$) than two hours ($p<0.01$), compared to CT alone (FIG. 1D). Furthermore, a high apoptotic index was apparent in both groups treated with DT01 and CT. Similar to other histological parameters, the extent of apoptosis was elevated in animals treated with a four-hour delay ($p<0.0001$). These histological findings were not apparent in the DT01 or chemotherapy alone treated groups.

For many solid tumors, proliferation and microvascularization are indispensable prerequisites for tumor development and metastasis. To further investigate these parameters, immunostaining for Ki67 and CD31, markers of cell proliferation and angiogenesis respectively, were performed in the viable tumor component (FIGS. 1E, 1F). Ki67 immunoreactivity indicated that tumors treated with either DT01 or chemotherapy alone were densely packed with a high degree of proliferation. Treatment with a two-hour interval between DT01 and CT resulted in a moderate decrease in proliferating cells (p=0.02) (FIG. 1E). Strikingly, immunoreactivity of Ki67 was 10-fold reduced in the group treated with a four-hour interval between DT01 and CT (p<0.001) (FIG. 1E). In this group, immunoreactivity was detected only in the tumor rim due to the high degree of necrosis observed in the center core region of the tumor. In addition, diminished intratumoral vessel densities were detected in groups treated with a combination of DT01 and CT, compared to CT alone (FIG. 1F). However, the mean microvessel density was even more notably reduced in the group treated with a four-hour interval (p<0.001) compared to two hours (p=0.02). Despite similarities in the anti-tumor effect on tumor growth at both the two and four-hour treatment schedules, histologically the efficacy was significantly more pronounced at the four-hour time point, in terms of necrosis, apoptosis, proliferation and angiogenesis.

Unexpectedly, tumors treated with a delay of four hours between DT01 and CT and sampled 22 days post treatment presented with a proportion of lysed hepatocytes within the tumor and slight edema in the adjacent non-malignant liver, in the absence of further clinical signs of toxicity such as loss of weight. Histological analyses did not reveal morphological signs of toxicity in the other groups (FIG. 1). In addition, liver enzyme tests did not reveal significant differences between the control and the combination treated groups.

Interestingly, no further edema was observed when animals receiving the same treatment were sacrificed between 30-65 days. This suggests that the edema observed at day 22, is reversible over time. Despite the significant tumor efficacy observed 22 days post treatment, tumors monitored after this time point resumed progression. Histological analysis revealed that the proliferative component reached ~50% at 30-45 days post treatment, only slightly below the level observed in non-treated tumors.

To confirm that combination treatment did not induce additional toxicity to the liver, the inventors analyzed the tolerability of DT01 in association with OXA or 5-FU for extended treatment cycles. They determined the toxicity of escalating doses of DT01 (total doses of 30, 50 or 80 mg) following systemic administration for two cycles (5×DT01 administrations per treatment cycle) associated to OXA or 5-FU in a cohort of 50 mice. No loss of weight was observed in animals during or post treatment. Similarly, other clinical signs of toxicity such as diarrhea or behavioral changes were not noted in these mice. At autopsy 6 weeks post the second cycle of treatment, all abdominal organs, the thoracic cavity and contents appeared normal. No major variations in liver weights or histology were observed between the vehicle and combination treated groups.

These results suggest that the reversible edema detected after combined treatment in animals bearing hepatic tumor is likely an acute reaction to the tumor response to efficient combination treatment.

Peritoneal Metastasis Treatment

Figure 2:
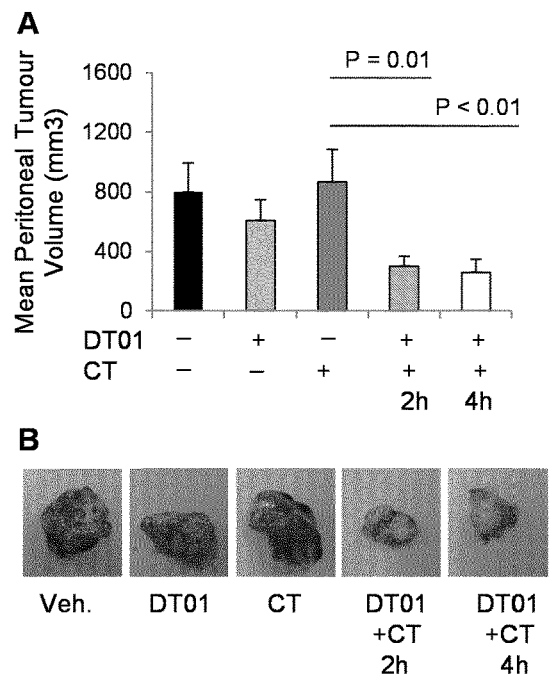
FIG. 2: Association of DT01 with CT significantly decreases the peritoneal tumor volume Intrahepatic tumor bearing NMRI$^{NU/NU}$ mice were treated as described in FIG. 4, and sacrificed 22 days post treatment. The presence of peritoneal metastasis was visually monitored during the duration of treatment and measured at the time of sacrifice. (A) Mean peritoneal tumor volume (mm$^3$) in each treatment group. (B) Representative macroscopic images of peritoneal tumors in each group. Results are expressed as an average±SEM.

CRC often metastasizes to the liver and the peritoneum. Interestingly 90% of the mice intrahepatically xenografted with CRC tumors developed peritoneal metastasis. This property allowed the inventors to monitor the effect of DT01 not only on liver tumors but also on peritoneal metastasis. Animals receiving a combination of DT01 and chemotherapy displayed significantly decreased peritoneal tumor volumes when compared to chemotherapy alone at both the two (mean volume: 300.31 vs 867.20 mm$^2$, respectively, p<0.01) and four hour time intervals (mean volume: 259.51 vs 867.20 mm$^2$, respectively, p<0.01) (FIG. 2A, 2B). Although a slight decrease in tumor volume was observed in the group treated with DT01 alone, this did not reach statistical significance.

Discussion

Approximately 50% of patients with CRC will present either with liver and/or peritoneal metastases or develop them throughout the course of their disease. A majority of patients with CRC hepatic metastases present with non-resectable disease and systemic chemotherapy represents the main if not the only form of therapy. However, the therapeutic window of chemotherapy is limited due to tumor resistance and high toxicity to non-targeted tissue. In such clinical situations, an aggressive chemotherapy regimen alone may not only fail to improve survival, but may also adversely affect the quality of life. Consequently the mortality of these patients remains high. Therefore development of new agents' specifically targeting DNA repair to circumvent chemoresistance and sparing healthy tissues is imperative in the treatment of these cancers. DT01 is an attractive drug candidate based on its central role in DNA repair.

In the present study, the inventors showed for the first time that systemic DT01 treatment sensitizes CRC cells to conventional chemotherapies by in vitro and in vivo assays. In a CRC metastatic model, they demonstrated significant anti-tumor efficacy in the liver and the peritoneum (regarded as a terminal condition) with DT01 treatment in combination with OXA and 5-FU. It is of interest to note, that the significant anti-tumor effect was limited to DT01 association with both OXA and 5-FU and not with single agent chemotherapy. This demonstrates that in agreement with the clinical conventional setting, combination with DT01 must be associated to double chemotherapy rather than single-agent chemotherapy in the treatment of CRC metastases. This study further highlights that tumors receiving double chemotherapy combined with DT01 restart proliferation and re-growth at later time points (post 22 days). Therefore repeated cycles of treatment would be necessary to achieve long term disease control similar to current conventional chemotherapy protocols. This would be possible as no added toxicity was observed with DT01 alone or in combination with OXA or 5-FU.

DT01 preferentially accumulate in the liver and intestines after systemic injection. Although the entire liver appeared to be uniformly fluorescent after Cy5-DT01 injection, the activation of DNA-PK revealed by the phosphorylation of H2AX was observed exclusively in tumor cells and not in the healthy tissue surrounding the tumor. This observation indicates that either DT01 does not enter non-tumor cells and/or that DT01 is not active in healthy liver tissue. DT01 was specifically designed by cholesterol conjugation firstly, in order to increase the bioavailability and secondly, to play on the difference in the substrate uptake between cancer and normal cells. Low density lipoproteins (LDL) are a major component of the cholesterol pathway. High requirement for LDL by malignant cells and thus the consequent overexpression of LDL receptors has been shown in many types of cancer cells making tumor cells specific targets of DT01. Additionally, an extensive analysis of normal and cancerous human tissues by immunohistochemistry revealed that either DNA-PKcs or Ku80 were consistently absent in the liver and the mammary epithelium, a specific post-transcriptional regulation that was not found in the other tissues and most of the tumors. Taken together, these data highlight that DT01 is likely to be an efficient drug for the treatment of liver cancers.

In conclusion, there is an urgent need for new treatment options targeting secondary hepatic malignancies, a rapidly progressive disease with a poor prognosis and an alarming rate of mortality. The present study demonstrated that combining systemic administration of DT01 with conventional chemotherapy can be a safe and effective therapeutic strategy in the treatment of CRC metastasis of the liver and the peritoneum.

Materials and Methods

Cell Culture, Constructs, Dbait Molecules, Immunofluorescence and Western Blotting CRC cell lines; HT29 (mutated p53, ATCC: HTB-38) and HCT116 (wild-type p53, ATCC: CCL-247) were purchased directly from ATCC. These cells were authenticated by ATCC by generating human short tandem repeat profiles by simultaneously amplifying multiple STR loci and amelogenin (for gender determination) using the Promega PowerPlex® Systems. These cells were cultured in the laboratory for less than 6 months from the date of purchase in DMEM medium supplemented with 10% fetal bovine serum, 1% sodium pyruvate, 100 mg/ml streptomycin and 100 mg/ml penicillin (Invitrogen, Carlsbad, Calif.), when the current study was performed. HT29 cell line stably expressing luciferase was established in-house using a pGL4.5 luciferase reporter vector (luc2/CMV/Hygro) (Promega). HT29 luciferase cells were supplemented with 200 µg/ml hygromycin B. All cell lines were additionally subjected to *mycoplasma* testing in-house and were free of *mycoplasma* contamination (Biovalley, France).

Cells were transfected with 2.5 µgs of Dbait (5'-G̲C̲T̲GTGCCCACAACCCAGCAAACAAGCCTAGA-(H)TCTAGGCTTGTTTGCTGGGTTGTGGGCACA̲G̲C̲-3' SEQ ID No 9) (Eurogentec, Belgium) where H is a hexaethyleneglycol linker and underlined nucleotides are phosphorothioates. The cells were sham transfected with an 8 bp oligonucleotide control (8H) complexed with 11 kDa polyethyleneimine (PEI) as previously described (Quantz et al, 2009, PloS one, 4, e6298).

γH2AX immunofluorescence was performed as described previously using a monoclonal anti-phospho-Histone H2A.X (Ser139) Antibody, clone JBW301 (1:500 dilution; 05-636, Millipore, USA) (9).

In Vitro Proliferation Assay

Cells were seeded at a density of $3\times10^4$ cells/60 mm dishes and transfected with Dbait. Following treatment, cells were washed and left untreated or treated with a combination of 5 µM of oxaliplatin (OXA, Sigma) and 2.5 µM of 5-fluouracil (5-FU, Sigma) and live cell counts were performed on days 1, 3, 5, 6, 7 and 9.

Clonogenic Assay

Cells were transfected with Dbait and left untreated or treated with 5 µM of OXA and 2.5 µM of 5-FU for 1 hr. The cells were diluted, allowed to grow for 14 days and the clones were stained with crystal violet and counted.

In Vivo Experiments

The current study was carried out in strict accordance with the European Union guidelines for animal care. All animal experimentation was approved by the ethics committees of the Institut Curie and the French ministry. Surgical procedures were performed under anesthesia with local analgesia to minimize suffering.

Animals

Six week old female NMRI$^{NU/NU}$ mice (Janvier, France) weighing 20-22 g were housed in specific pathogen free environment on a 12 h light and 12 h dark schedule with food and water ad libitum. No more than 6 animals were housed per cage and they were acclimated for at least one week prior to initiating in vivo studies.

Intrahepatic HT29L Grafting

HT29 Luciferase (HT29L) cells were implanted by direct injection of cell suspensions ($1\times10^6$/10 µL of PBS) onto the upper surface of the left lobe. Tumor growth was monitored through bioluminescence analysis (IVIS, Caliper sciences).

DT01 Molecule

For in vivo studies, DT01 (Dbait with a cholesterol tetraethylene glycol incorporated at the 5'-end) was used (Agilent technologies, Boulder, Colo.).

Pharmacokinetics of DT01

HT29L grafted mice were treated with a single intraperitoneal (IP, n=4) or intravenous (IV, n=3) injection of 5 mg of DT01. Blood samples were harvested prior to treatment and 1, 5, 10, 30 mins, 1 hr, 2 hrs, 4 hrs and 6 hrs post treatment. Plasma was recovered through centrifugation and assayed by ELISA.

Fluorescence Measurement of Organs

As the ELISA technique failed to produce reliable quantification in tissues, we used fluorescent imaging, a reliable technique for assessing molecule distribution (15). NMRI$^{NU/NU}$ mice were injected with 1 mg of the DT01 fluorescent molecule (DT01-Cy5) through IP (n=3) or IV (n=3) administration. The fluorescent DT01 (DT01-Cy5) incorporates a cyanine 5 at the thymidine located immediately after the linker. Six hours after injection, fluorescence imaging was performed using a Typhoon scanner (GE Helatcare).

DT01 and Chemotherapy Treatment

HT29L grafted animals (n=49) were allocated into treatment groups and administered one cycle of treatment. DT01 was systemically administered through IP injection at a dose of 5 mgs/day for 5 consecutive days starting on day 0 (DO). OXA (6 mg/kg, 1× per cycle, Day 1) and 5-FU (25 mg/kg, 3× per cycle, Days 1-3) were administered 2 or 4 hours after DT01 treatment. These mice were sacrificed 22 days post treatment.

An additional group treated with DT01 and OXA/5-FU at the 4 hour interval (n=10) were kept after treatment until the termination guidelines were met to assess the duration of treatment efficacy.

Liver Function Assessment

Blood samples were obtained through submandibular bleeding in lithium heparin tubes (Sarstedt) on days 0, 4 and 18 post treatment. Plasma alanine transaminase (ALT), aspartate aminotransferase (ASAT), alkaline phosphatase (ALP), glutamyl transpeptidase (GGT), amylase (AMYL) and total bilirubin (TBIL) were measured using an MS-Scan II (Melet Schloesing Laboratories, France).

Toxicity Assays

NMRI$^{NU/NU}$ mice (n=50) were treated with two cycles of DT01 at escalating doses of 3 mg/day (30 mg total), 5 mg/day (50 mg total) or 8 mg/day (80 mg total) through IP injection in combination with OXA or 5'-FU. OXA and 5'-FU were administered through systemic IP injection at doses of 1×6 mg/kg or 3×25 mg/kg, 4 hours after DT01 treatment respectively. Animals were observed regularly for any adverse effects.

Histology

Hematoxylin, eosin, and saffron (HES) stained tumor sections were assessed by an experienced pathologist (Dr. Huerre, Institut Curie) in a blinded fashion. Viable and necrotic components (indicated by increased cell size, indistinct cell border, eosinophilic cytoplasm, loss or condensation of the nucleus, or associated inflammation) were expressed as a proportion (%) of the total tumor surface.

Apoptosis was estimated (weak-<5%, moderate 5-10%, significant 10-20% and very significant 20-50%) from representative non-necrotic fields at high power.

Digitization and image capture was performed using a whole-slide scanning system (Philips digital pathology solutions).

Ki67 and CD31 Immunohistochemistry

Immunohistochemistry was performed using rabbit anti-Ki67 (ab28364, 1/500; Abcam, UK) and rabbit anti-CD31 (ab15580, 1/500; Abcam, UK) antibodies. This was followed by a secondary biotinylated goat anti-rabbit IgG antibody (BA-1000; Vector, USA) and revealed using a rabbit specific HRP/DAB (ABC) detection kit. Images were captured using a fluorescence microscope (Eclipse 90i, Nikon). The average Ki67 index was scored by establishing a ratio between Ki67+ve and –ve cells, in five randomly selected microscopic fields per section. Average microvessel density was determined by CD31 staining. CD31 positive vessels were counted in five randomly selected microscopic fields per section.

Statistical Analysis

In vitro experiments were performed with a minimum of two independent experiments. Two-sided unpaired t-tests were used for comparison of cell mortality and survival. Kruskal-Wallis tests were used to compare tumor volumes, and histological data. Error bars indicate standard error of the mean (SEM), except when specifically indicated. All statistical analyses were performed using StatEL software (adScience, France) and a P value of 0.05 was considered statistically significant.

Example 2: DT01 in Models of Triple Negative Breast Cancer (TNBC) and its Potentiating Effect in a Co-Treatment with Carboplatin DT01 Effect Alone on a TNBC Model The objective of the present study was to demonstrate a systemic effect of DT01 alone in a model of breast cancer, in particular of triple negative breast cancer. The animal model is mice after 45 days of engraftment. Mice were subcutaneously grafted in mammary fat pad with MDA-MB-231 tumor cells.

In previous experiments, the inventors demonstrated that DT01 could control effectively tumor growth in all tested triple negative breast cancer models (mice engrafted with BC227, BC173, MDA-MB-468 and MDA-MB-231 cell lines) by local administration.

Figure 3:
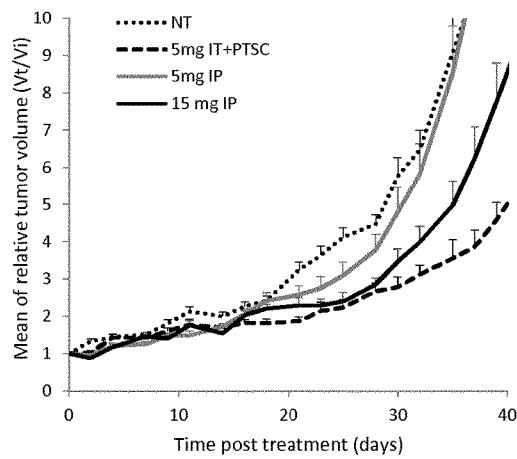
FIG. 3: Comparison of systemic and local administration in two TNBC xenografted models. NMRI$^{NU/NU}$ mice grafted in the fat pad with TNBC cell lines were treated by SC or IP injections of Dbait during 5 consecutive days for one cycle (left panel) or three cycles (right panel) separated each by two weeks without treatment. Doses of each Dbait injection is indicated in the legend. The Data represent the mean relative tumor volume (Vt/Vi) at the different time after beginning of treatment.
Figure 3:
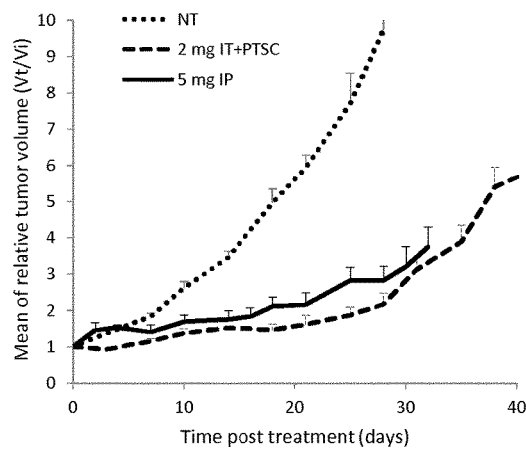

As shown in FIG. 3, the inventors compared intraperitoneal administration to local administration (intratumoral and peri-tumoral subcutaneous) in two TNBC xenografted models. They surprisingly observed that 3-5 fold more DT01 are required for similar efficacy than local administration.

The route of administration was intraperitoneal administration which mimics in mouse intravenous perfusion administration in human. The dose level of DT01 was 5 mg/animal/day. The DT01 intraperitoneal administration was performed during 3 sessions of 5 consecutive days with one week without treatment between each cycle. 13 mice were included, 7 of which receiving DT01. The control group received vehicle alone 0.9% NaCl.

No toxicity was observed. Intraperitoneal DT01 administration is well tolerated.

DT01 treatment showed a significant better tumor growth control and animal survival than the control group.

The MDA-MB-231 triple negative breast cancer model was chosen because it was the most resistant to DT01 treatment in previous experiments using intratumoral and peri-tumor subcutaneous administrations.

This experiment confirms that standalone administration of DT01 delays tumor growth in breast cancer tumor.

Effect of the Combination of DT01 with Carboplatin on a TNBC Model

Figure 6:
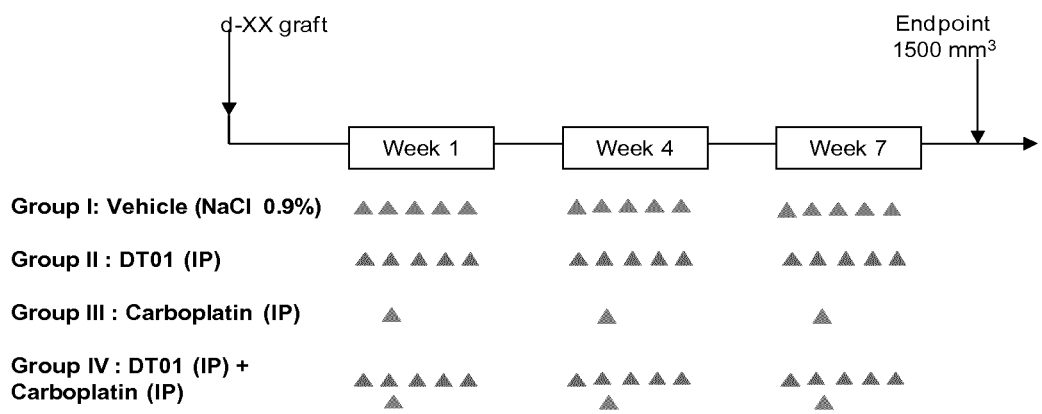
FIG. 6: Scheme of treatment in FIGS. 4 and 5.

As shown in FIG. 6, each treatment cycle comprised of 5 consecutive days of administration with DT01 at a dose level of 5 mg/animal/day. Treatment was administered in 3 cycles with a 2 week gap between cycles either alone or in association with carboplatin. Only one dose of carboplatin was injected per cycle of DT01 treatment ($2^{nd}$ day of each cycle). The dose of carboplatin was 50 mg/kg per cycle. Treatments were performed over 7 weeks (3 cycles of treatment).

During the experiment no toxicity is observed. No sign of toxicity such as loss of weight in DT01 treated group. No increase in weight loss or toxicity in DT01+ carboplatin treated group was observed compared to the carboplatin group.

No abnormal death occurred during the 177 days of the experiment, except one in the carboplatin alone treated group.

Intraperitoneal DT01 administration is well tolerated.

Antitumor activity was evaluated by measuring tumor volume during and after treatment. DT01 was administered intraperitoneally during 3 sessions of 5 days treatment with two weeks of rest between each session. Carboplatin was administered once a week on the second day of each DT01 treatment cycle.

Figure 4:
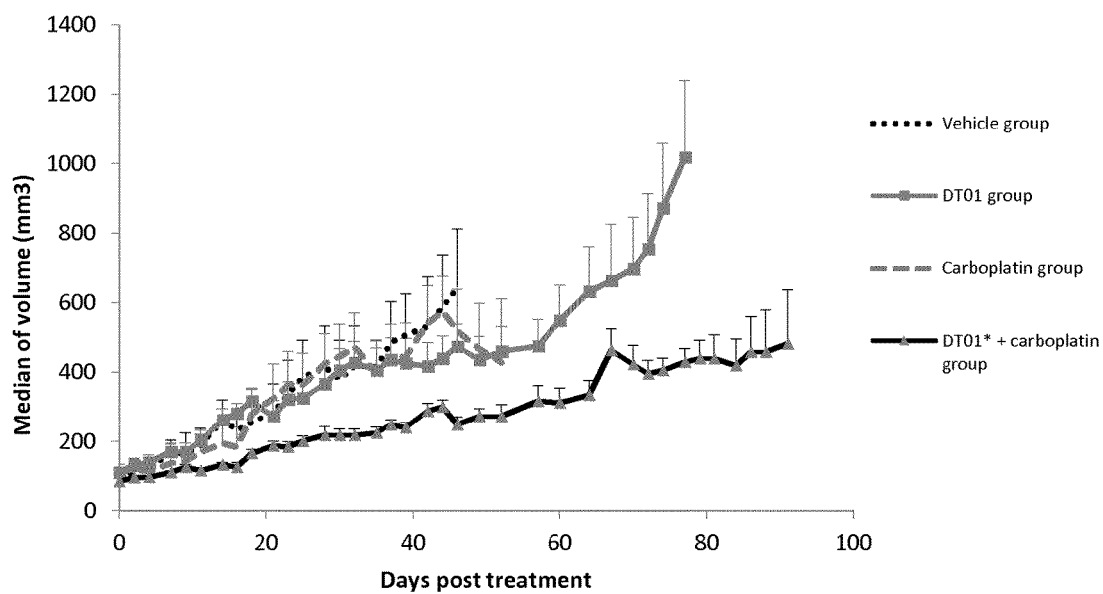
FIG. 4: DT01 association to carboplatin significantly decreases tumor growth in TNBC model. Median tumor volume per treatment group (error bars in DT01 treated group and DT01+ carboplatin group indicate the standard error of the mean, SEM).
Figure 5:
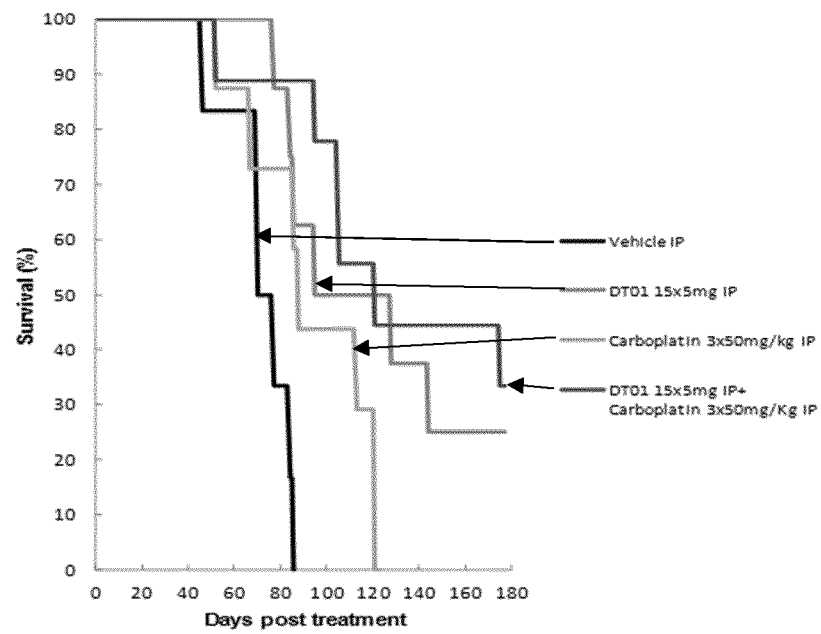
FIG. 5: DT01 association to carboplatin significantly increases survival in TNBC model. Kaplan-Meier representation of animal survival in MDA-MB-231 model.

DT01+ carboplatin combination treatment showed a better tumor growth control compared to DT01 standalone treatment (FIG. 4). The curve was discontinued on the day of the first death in each group. In addition, the DT01+ carboplatin combination also increases the survival.

In this study, the treatment of DT01 combining with carboplatin is efficient and leads to a better tumor growth delay than single treatments.

Materials and Methods

DT01 Molecule

DT01, the cholesterol tetraethylene glycol incorporated form of Dbait was synthesized by automated solid-phase oligonucleotide synthesis (Agilent technologies, USA).

Cells & Animals

The MDA-MB231 cell line is derived from a human breast adenocarcinoma and can be ordered at the ATCC. The MDA-MB231 cells were grafted in the mammary fat pad with $10 \cdot 10^6$ cells re-suspended in 0.1 ml of DMEM with no additive. The athymic nude mouse is immunodeficient, thus enabling the xenotransplantation and growth of human tumors.

The invention claimed is:

1. A method of treating triple-negative breast cancer (TNBC) or chemoresistant lung cancer comprising the administration, by a parenteral systemic route selected from intraperitoneal and intravenous administration to a subject having a triple-negative breast cancer (TNBC) or chemoresistant lung cancer, a nucleic acid molecule of the following formula:

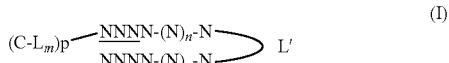
(I)

wherein N is a deoxynucleotide, n is an integer from 15 to 195, the underlined N refers to a nucleotide having or not a modified phosphodiester backbone, L' is a linker, C is the molecule facilitating endocytosis selected from a lipophilic molecule or a ligand which targets cell receptor enabling receptor mediated endocytosis, L is a linker, m is an integer being 0 or 1 and p is 1;

wherein the nucleic acid is to be used without combined administration of any quinoline endosomolytic agent.

2. The method according to claim 1, wherein the nucleic acid of formula (I) has one or several of the following features:

N is a deoxynucleotide selected from the group consisting of A (adenine), C (cytosine), T (thymine) and G (guanine) and selected so as to avoid occurrence of a CpG dinucleotide and to have less than 80% sequence identity to any gene in a human genome; and/or the linked L' is selected from the group consisting of hexaethyleneglycol, tetradeoxythymidylate (T4) and 1,19-bis(phospho)-8-hydraza-2-hydroxy-4-oxa-9-oxo-nonadecane; and/or m is 1 and L is a carboxamido polyethylene glycol; and/or C is selected from the group consisting of a cholesterol, single or double chain fatty acids and a ligand which targets cell receptor.

3. The method according to claim 1, wherein the nucleic acid molecule has one of the following formulae:

(Ia)

SEQ ID NO: 6

(Ib)

SEQ ID NO: 7

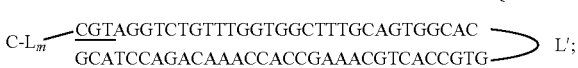

(Ic)

SEQ ID NO: 8

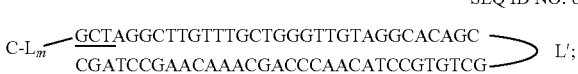

(Id)

SEQ ID NO: 9

C-L$_m$—GCTGTGCCCACAACCCAGCAAACAAGCCTAGA—L' and;
       CGACACGGGTGTTGGGTCGTTTGTTCGGATCT (Ie)

SEQ ID NO: 10

C-L$_m$—GCTAGGTCTGTTTGGTGGCTTTGCAGTGGCAC—L';
       CGATCCAGACAAACCACCGAAACGTCACCGTG wherein the underlined nucleotide refers to a nucleotide having or not a phosphorothioate or methylphosphonate backbone, the linked L' is selected from the group consisting of hexaethyleneglycol, tetradeoxythymidylate (T4) and 1,19-bis(phospho)-8-hydraza-2-hydroxy-4-oxa-9-oxo-nonadecane; m is 1 and L is a carboxamido oligoethylene glycol, C is selected from the group consisting of dioleoyl, octadecyl, folic acid, tocopherol and cholesterol.

4. The method according to claim 1, wherein the nucleic acid is (Id)

SEQ ID NO: 9

C-L$_m$—GCTGTGCCCACAACCCAGCAAACAAGCCTAGA—L'
       CGACACGGGTGTTGGGTCGTTTGTTCGGATCT and wherein the underlined nucleotide refers to a nucleotide having a phosphorothioate backbone, the linked L' is 1,19-bis(phospho)-8-hydraza-2-hydroxy-4-oxa-9-oxo-nonadecane; m is 1 and L is a carboxamido tetraethylene glycol, C is cholesterol.

5. The method according to claim 1, wherein the nucleic acid is to be administered by intravenous route.

6. The method according to claim 5, wherein the nucleic acid is to be administered by injection, intravenous drip, bolus or pump.

7. The method according to claim 1, wherein the TNBC is a platinum-resistant cancer.

8. The method according to claim 1, wherein the nucleic acid is administered in combination with radiotherapy and/or chemotherapy.

9. The method according to claim 1, wherein the nucleic acid is administered in combination with a DNA damaging agent.

10. The method according to claim 9, wherein the DNA damaging agent is selected from the group consisting of an inhibitor of topoisomerases I or II, a DNA crosslinker, a DNA alkylating agent, an anti-metabolic agent and inhibitors of the mitotic spindles.

11. The method according to claim 1, wherein the nucleic acid is to be used in combination with a platinum drug selected from the group consisting of oxaliplatin, carboplatin and cisplatin.

12. The method according to claim 2, wherein L is carboxamido triethylene or tetraethylene glycol.

13. The method according to claim 2, wherein C is selected from the group consisting of octadecyl, oleic acid, dioleoyl acid, stearic acid, tocopherol, cholesterol, folic acid, galactose, mannose, oligosaccharide of galactose and/or mannose, RGD, bombesin, integrin and transferrin.

* * * * *

UNITED STATES PATENT AND TRADEMARK OFFICE
CERTIFICATE OF CORRECTION

PATENT NO. : 10,821,128 B2
APPLICATION NO. : 16/081045
DATED : November 3, 2020
INVENTOR(S) : Marie Dutreix and Nathalie Berthault Page 1 of 1

It is certified that error appears in the above-identified patent and that said Letters Patent is hereby corrected as shown below:

In the Specification

Column 33,
Line 29, "of 0.05" should read --of ≤ 0.05--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 11

<210> SEQ ID NO 1
<211> LENGTH: 32

```
<212> TYPE: DNA
<213> ORGANISM: artificial sequence
<220> FEATURE:
<223> OTHER INFORMATION: Dbait32

<400> SEQUENCE: 1
acgcacgggt gttgggtcgt tgttcggat ct                                    32

<210> SEQ ID NO 2
<211> LENGTH: 32
<212> TYPE: DNA
<213> ORGANISM: artificial sequence
<220> FEATURE:
<223> OTHER INFORMATION: Dbait32Ha

<400> SEQUENCE: 2
cgtaggtctg tttggtggct ttgcagtggc ac                                    32

<210> SEQ ID NO 3
<211> LENGTH: 32
<212> TYPE: DNA
<213> ORGANISM: artificial sequence
<220> FEATURE:
<223> OTHER INFORMATION: Dbait32Hb

<400> SEQUENCE: 3
gctaggcttg tttgctgggt tgtaggcaca gc                                    32

<210> SEQ ID NO 4
<211> LENGTH: 32
<212> TYPE: DNA
<213> ORGANISM: artificial sequence
<220> FEATURE:
<223> OTHER INFORMATION: Dbait32Hc

<400> SEQUENCE: 4
gctgtgccca aacccagca aacaagccta ga                                    32

<210> SEQ ID NO 5
<211> LENGTH: 32
<212> TYPE: DNA
<213> ORGANISM: artificial sequence
<220> FEATURE:
<223> OTHER INFORMATION: Dbait32Hd

<400> SEQUENCE: 5
gctaggtctg tttggtggct ttgcagtggc ac                                    32

<210> SEQ ID NO 6
<211> LENGTH: 32
<212> TYPE: DNA
<213> ORGANISM: artificial sequence
<220> FEATURE:
<223> OTHER INFORMATION: nucleic acid molecule Ia
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
```

-continued

```
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 1,19-bis(phospho)-8-hydraza-2-hydroxy-4-
      oxa-9-oxo-nonadecane

<400> SEQUENCE: 6
acgcacgggt gttgggtcgt tgttcggat ct                                    32

<210> SEQ ID NO 7
<211> LENGTH: 32
<212> TYPE: DNA
<213> ORGANISM: artificial sequence
<220> FEATURE:
<223> OTHER INFORMATION: nucleic acid molecule Ib
<220> FEATURE:
<221> NAME/KEY: misc_feature
<222> LOCATION: (1)..(3)
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 1,19-bis(phospho)-8-hydraza-2-hydroxy-4-
      oxa-9-oxo-nonadecane

<400> SEQUENCE: 7
cgtaggtctg tttggtggct ttgcagtggc ac                                   32

<210> SEQ ID NO 8
<211> LENGTH: 32
<212> TYPE: DNA
<213> ORGANISM: artificial sequence
<220> FEATURE:
<223> OTHER INFORMATION: nucleic acid molecule Ic
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
```

```
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 1,19-bis(phospho)-8-hydraza-2-hydroxy-4-
      oxa-9-oxo-nonadecane

<400> SEQUENCE: 8
gctaggcttg tttgctgggt tgtaggcaca gc                                      32

<210> SEQ ID NO 9
<211> LENGTH: 32
<212> TYPE: DNA
<213> ORGANISM: artificial sequence
<220> FEATURE:
<223> OTHER INFORMATION: nucleic acid molecule Id
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 1,19-bis(phospho)-8-hydraza-2-hydroxy-4-
      oxa-9-oxo-nonadecane

<400> SEQUENCE: 9
gctgtgccca caacccagca aacaagccta ga                                      32

<210> SEQ ID NO 10
<211> LENGTH: 32
<212> TYPE: DNA
<213> ORGANISM: artificial sequence
<220> FEATURE:
<223> OTHER INFORMATION: nucleic acid molecule Ie
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 1,19-bis(phospho)-8-hydraza-2-hydroxy-4-
```

```
    oxa-9-oxo-nonadecane

<400> SEQUENCE: 10
gctaggtctg tttggtggct ttgcagtggc ac                                32

<210> SEQ ID NO 11
<211> LENGTH: 32
<212> TYPE: DNA
<213> ORGANISM: artificial sequence
<220> FEATURE:
<223> OTHER INFORMATION: nucleic acid molecule DT01
<220> FEATURE:
<221> NAME/KEY: misc_feature
<223> OTHER INFORMATION: note="at the 3' end of the complementary strand
      the three last nucleotides with phosphorothioate backbone"
<220> FEATURE:
<221> NAME/KEY: misc_feature
<222> LOCATION: (1)..(1)
<223> OTHER INFORMATION: at the 5' end,
      10-O-[1-propyl-3-N-carbamoylcholesteryl]-tetraethyleneglycol
      radical
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =
      2,19-bis(phosphor)-8-hydraza-1-hydroxy-4-oxa-9-oxo-nonadecane

<400> SEQUENCE: 11
gctgtgccca acccagca aacaagccta ga                                  32
```